United States Patent [19]
Castro Pineiro et al.

[11] Patent Number: 6,048,878
[45] Date of Patent: Apr. 11, 2000

[54] SUBSTITUTED PIPERIDINE DERIVATIVES AS SELECTIVE AGONISTS OF 5-HT RECEPTORS

[75] Inventors: Jose Luis Castro Pineiro, Bishops Stortford; Ian James Collins, Ware; Angus Murray MacLeod, Bishops Stortford; Christopher Richard Moyes, Sawbridgeworth; Michael Rowley, Harlow; Graham Andrew Showell, Bury St. Edmunds, all of United Kingdom

[73] Assignee: Merck Sharp & Dohme Ltd., Hoddesdon, United Kingdom

[21] Appl. No.: 09/068,752

[22] PCT Filed: Nov. 13, 1996

[86] PCT No.: PCT/GB96/02765

§ 371 Date: May 13, 1998

§ 102(e) Date: May 13, 1998

[87] PCT Pub. No.: WO97/18202

PCT Pub. Date: May 22, 1997

[30] Foreign Application Priority Data

Nov. 16, 1995 [GB] United Kingdom ............... 9523460

[51] Int. Cl.[7] .................... A61K 31/445; C07D 401/14
[52] U.S. Cl. ................................... 514/323; 546/201
[58] Field of Search .................... 546/201; 514/323

[56] References Cited

FOREIGN PATENT DOCUMENTS

94/02477  2/1994  WIPO .
94/21627  9/1994  WIPO .
96/04274  2/1996  WIPO .

OTHER PUBLICATIONS

Cram and Hammond, "Organic Chemistry", McGraw–Hill Book Co., NY (1964) 2nd Ed. pp. 565–567.

*Primary Examiner*—Patricia L. Morris
*Attorney, Agent, or Firm*—James L. McGinnis; David L. Rose

[57] ABSTRACT

A compound of formula (I), or a salt or prodrug thereof, is described, wherein G is attached at position 3 or 4 of the piperidine ring and represents halogen or $C_{1-6}$ alkoxy; R1 represents $C_{3-6}$ alkenyl, $C_{3-6}$ alkynyl, aryl($C_{1-6}$)alkyl or heteroaryl ($C_{1-6}$)alkyl, any of which groups may be optionally substituted; processes for its preparation and its use in therapy, particularly in the treatment of migraine.

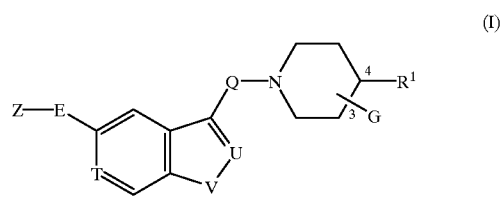

(I)

5 Claims, No Drawings

SUBSTITUTED PIPERIDINE DERIVATIVES AS SELECTIVE AGONISTS OF 5-HT RECEPTORS

The present invention relates to a class of substituted piperidine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol 1, 1309-11; and W. Feniuk and P. P. A. Humphrey, *Drug Development Research*, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D_\alpha}$ (or 5-HT$_{1D-1}$) and 5-HT$_{1D_\beta}$ (or 5-HT$_{1D-2}$), and their amino acid sequences are disclosed and claimed in WO-A-91117174.

The 5-HT$_{1D_\alpha}$ receptor subtype in humans is believed to reside on sensory terminals in the dura mater. Stimulation of the 5-HT$_{1D_\alpha}$ subtype inhibits the release of inflammatory neuropeptides which are thought to contribute to the headache pain of migraine. The human 5-HT$_{1D_\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.*, 1992, 304, 1415; J. P. Ottervanger et al., *The Lancet*, 1993, 341, 861–2: and D. N. Bateman, *The Lancet*. 1993, 341, 221–4). Since sumatriptan barely discriminates between the human 5-HT$_{1D_\alpha}$ and 5-HT$_{1D_\beta}$ receptor subtypes (cf. WO-A-91/17174, Table 1), and since it is the blood vessels with which the 5-HT$_{1D_\beta}$ subtype is most closely associated, it is believed that the cardiovascular side-effects observed with sumatriptan can be attributed to stimulation of the 5-HT$_{1D_\beta}$ receptor subtype. It is accordingly considered (cf. G. W. Rebeck et al., *Proc. Natl. Acad. Sci. USA*, 1994, 91, 3666–9) that compounds which can interact selectively with the 5-HT$_{1D_\alpha}$ receptor subtype, whilst having a less pronounced action at the 5-HT$_{1D_\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D_\alpha}$ receptor subtype. Moreover, the compounds in accordance with this invention have been found to possess at least a 10-fold selective affinity for the 5-HT$_{1D_\alpha}$ receptor subtype relative to the 5-HT$_{1D_\beta}$ subtype, and they can therefore be expected to manifest fewer side-effects than those associated with non-subtype-selective 5-HT$_{1D}$ receptor agonists.

Several distinct classes of substituted five-membered heteroaromatic compounds are described in published European patent applications 0438230, 0494774 and 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the piperidine derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the substituted piperazine moiety with a differently substituted piperidine moiety.

WO-A-91/18897 describes a class of tryptamine derivatives substituted by various five-membered rings, which are stated to be specific to a particular type of "5-HT$_1$-like" receptor and thus to be effective agents for the treatment of clinical conditions, particularly migraine, requiring this activity. A further class of tryptamine derivatives with alleged anti-migraine activity is disclosed in WO-A-94/02460. However, neither WO-A-91118897 nor WO-A-94102460 discloses or suggests the piperidine derivatives provided by the present invention.

Moreover, nowhere in the prior art mentioned above is there any disclosure of a subtype-selective 5-HT$_{1D}$ receptor agonist having a 5-HT$_{1D_\alpha}$ receptor binding affinity (IC$_{50}$) below 50 nM and at least a 10-fold selective affinity for the 5-HT$_{1D_\alpha}$ receptor subtype relative to the 5-HT$_{1D_\beta}$ subtype.

The compounds according to the present invention are subtype-selective 5-HT$_{1D}$ receptor agonists having a human 5-HT$_{1D_\alpha}$ receptor binding affinity (IC$_{50}$) below 50 nM, typically below 10 nM and preferably below 1 nM; and at least a 10-fold selective affinity, typically at least a 50-fold selective affinity and preferably at least a 100-fold selective affinity, for the human 5-HT$_{1D_\alpha}$ receptor subtype relative to the 5-HT$_{1D_\beta}$ subtype. Moreover, the compounds in accordance with this invention possess interesting properties in terms of their efficacy and/or bioavailability.

The present invention provides a compound of formula I, or a salt or prodrug thereof:

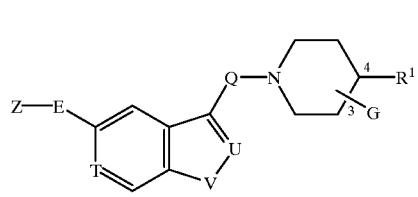

(I)

wherein

Z represents hydrogen, halogen, cyano, nitro, trifluoromethyl —OR$^5$, —OCOR$^5$, —OCONR$^5$R$^6$, —OCH$_2$CN, —OCH$_2$CONR$^5$R$^6$, —SR$^5$, —SOR$^5$, —SO$_2$R$^5$, —SO$_2$NR$^5$R$^6$, NR$^5$R$^6$, —NR$^5$COR$^6$, —NR$^5$CO$_2$R$^6$, —NR$^5$SO$_2$R$^6$, —COR$^5$, —CO$_2$R$^5$, —CONR$^5$R$^6$, or a group of formula (Za), (Zb), (Zc) or (Zd):

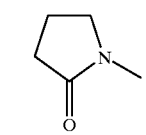
(Za)

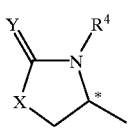
(Zb)

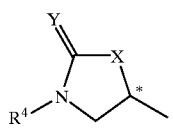
(Zc)

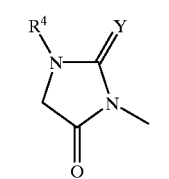
(Zd)

in which the asterisk * denotes a chiral centre; or

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

X represents oxygen, sulphur, —NH— or methylene;

Y represents oxygen or sulphur;

E represents a chemical bond or a straight or branched alkylene chain containing from 1 to 4 carbon atoms;

Q represents a straight or branched alkylene chain containing from 1 to 6 carbon atoms, optionally substituted in any position by one or more substituents selected from fluoro and hydroxy;

T represents nitrogen or CH;

U represents nitrogen or C-$R^2$;

V represents oxygen, sulphur or N-$R^3$;

G is attached at position 3 or 4 of the piperidine ring and represents halogen or $C_{1-6}$ alkoxy;

$R^1$ represents $C_{3-6}$ alkenyl, $C_{3-6}$ alkynyl, aryl($C_{1-6}$)alkyl or heteroaryl($C_{1-6}$)alkyl, any of which groups may be optionally substituted;

$R^2$, $R^3$ and $R^4$ independently represent hydrogen or $C_{1-6}$ alkyl; and $R^5$ and $R^6$ independently represent hydrogen, $C_{1-6}$ alkyl, trifluoromethyl, phenyl, methylphenyl, or an optionally substituted aryl($C_{1-6}$)alkyl or heteroaryl($C_{1-6}$)alkyl group; or $R^5$ and $R^6$, when linked through a nitrogen atom, together represent the residue of an optionally substituted azetidine, pyrrolidine, piperidine, morpholine or piperazine ring.

Where Z in the compounds of formula I above represents a five-membered heteroaromatic ring, this ring may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include $C_{1-6}$ alkyl, $C_{2-6}$ alkenyl, $C_{2-6}$ alkynyl, $C_{3-7}$ cycloalkyl, aryl, aryl($C_{1-6}$) alkyl, $C_{3-7}$ heterocycloalkyl, heteroaryl, heteroaryl($C_{1-6}$) alkyl, $C_{1-6}$ alkoxy, $C_{1-6}$ alkylthio, amino, $C_{1-6}$ alkylamino, di($C_{1-6}$)alkylamino, halogen, cyano and trifluoromethyl.

The group $R^1$ may be optionally substituted by one or more substituents, as also may the groups $R^5$ or $R^6$ where these represent aryl($C_{1-6}$)alkyl or heteroaryl($C_{1-6}$)alkyl. $R^1$ may be unsubstituted. $R^1$ may be substituted Where $R^1$, $R^5$ or $R^6$ represents aryl($C_{1-6}$)alkyl or heteroaryl($C_{1-6}$)alkyl, any optional substitution will suitably be on the aryl or heteroaryl moiety thereof, although substitution on the alkyl moiety thereof is an alternative possibility. Examples of optional substituents thereon include halogen, cyano, trifluoromethyl, triazolyl, tetrazolyl, $C_{1-6}$ alkyl-tetrazolyl, hydroxy, $C_{1-6}$ alkoxy, $C_{1-6}$ alkylthio, $C_{2-6}$ alkoxycarbonyl, $C_{2-6}$ alkylcarbonyl, $C_{1-6}$ alkylsulphonyl arylsulphonyl, amino, $C_{1-6}$ alkylamino, di($C_{1-6}$)alkylamino, di($C_{1-6}$) alkylaminomethyl, $C_{2-6}$ alkylcarbonylamino, arylcarbonylamino, $C_{2-6}$ alkoxycarbonylamino, N-($C_{1-6}$) alkyl-N-($C_{2-6}$)alkoxycarbonylamino, $C_{1-6}$ alkylsulphonylamino, arylsulphonylamino, $C_{1-6}$ alkylsulphonylaminomethyl, aminocarbonylamino, $C_{1-6}$ alkylaminocarbonylamino, di($C_{1-6}$) alkylaminocarbonylamino, mono- or diarylaminocarbonylamino, pyrrolidinylcarbonyiamino, piperidinylcarbonylamino, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$) alkylaminosulphonyl, aminosulphonylmethyl, $C_{1-6}$ alkylaminosulphonylmethyl and di($C_{1-6}$) alkylaminosulphonylmethyl.

When $R^5$ and $R^6$, when linked through a nitrogen atom, together represent the residue of an azetidine, pyrrolidine, piperidine, morpholine or piperazine ring, this ring may be unsubstituted or substituted by one or more substituents. Examples of suitable substituents include $C_{1-6}$ alkyl, aryl ($C_{1-6}$)alkyl, $C_{1-6}$ alkoxy, $C_{2-6}$ alkoxycarbonyl and $C_{1-6}$ alkylaminocarbonyl. Typical substituents include methyl, benzyl, methoxy, methoxycarbonyl, ethoxycarbonyl and methylaininocarbonyl. In particular, where $R^5$ and $R^6$ together represent the residue of a piperazine ring, this ring is preferably substituted on the distal nitrogen atom by a $C_{2-6}$ alkoxycarbonyl moiety such as methoxycarbonyl or ethoxycarbonyl.

As used herein, the expression "$C_{1-6}$ alkyl" includes methyl and ethyl groups, and straight-chained or branched propyl butyl, pentyl and hexyl groups. Particular alkyl groups are methyl ethyl, n-propyl, isopropyl and t-butyl. Derived expressions such as "$C_{1-6}$ alkoxy", "$C_{1-6}$ alkylthio" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl, allyl dimethylallyl and butenyl groups.

The expression "$C_{2-6}$ alkynyl" as used herein refers to straight-chained and branched alkynyl groups containing from 2 to 6 carbon atoms. Typical examples include ethynyl and propargyl groups.

Typical $C_{3-7}$ cycloayl groups include cyclopropyl, cyclobutyl, cyclopentyl and cyclohexyl.

Typical aryl groups include phenyl and naphthyl.

The expression "aryl($C_{1-6}$)alkyl" as used herein includes benzyl phenylethyl, phenylpropyl and naphthylmethyl. As mentioned above the alkyl group may be straight or branched.

Suitable heterocycloalkyl groups include azetidinyl pyrrolidyl, piperidyl, piperazinyl and morpholinyl groups.

Suitable heteroaryl groups include pyridyl, quinolyl, isoquinolyl pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimindazolyl oxadiazolyl, thiadiazolyl triazolyl and tetrazolyl groups.

The expression "heteroaryl($C_{1-6}$)alkyl" as used herein includes furylmethyl, furylethyl, thienylmethvl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl triazolylethyl, tetrazolylmethyl, tetrazolylethyl, pyridylmethyl, pyridylethyl, pyrimidinylmethyl, pyrazinylmethyl, quinolylmethyl and isoquinolylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. For example, the compounds of formula I above wherein Z represents a group of formula (Zb) or (Zc) have a chiral centre denoted by the asterisk *, which may accordingly be in the (R) or (S) configuration. It is to be understood that all such isomers and mixtures thereof in any proportion are encompassed within the scope of the present invention.

Where E and Q, which may be the same or different, represent straight or branched alkylene chains, these may be, for example, methylene ethylene, 1-methylethylene, propylene, 2-methylpropylene or butylene. In addition, the alkylene chain Q may be substituted in any position by one or more substituents selected from fluoro and hydroxy giving rise, for example, to a 2-hydroxypropylene, 2-hydroxymethylpropylene, 2-fluoropropylene or 2-fluoromethyl-propylene chain Q. Moreover, E may represent a chemical bond such that the moiety Z is attached directly to the central fused bicyclic heteroaromatic ring system containing the variables T, U and V.

Suitably, E represents a chemical bond or a methylene linkage.

Representative alkylene chains for Q include propylene, butylene, 2-hydroxypropylene, 2-hydroxymethyl- propylene, 2-fluoropropylene and 2-fluoromethyl-propylene, especially propylene.

The compound of formula I in accordance with the present invention is suitably an indole, benzofuran or benzthiophene derivative of formula IA, an indazole derivative of formula IB, or a pyrrolo[2,3-c]pyridine derivative of formula IC:

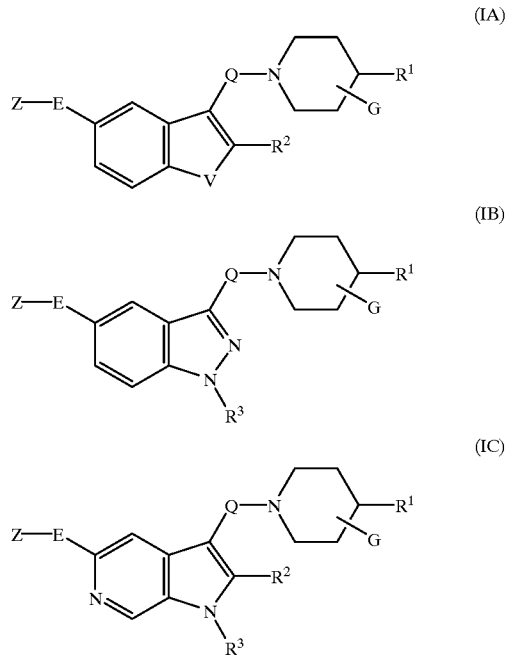

wherein Z, E, Q, V, G, $R^1$, $R^2$ and $R^3$ are as defined above. Preferably, the compounds according to the invention are indole or pyrrolo[2,3-c]pyridine derivatives of formula ID:

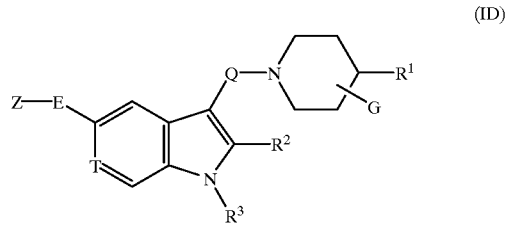

wherein Z, E, Q, T, G, $R^1$, $R^2$ and $R^3$ are as defined above, in particular wherein $R^2$ and $R^3$ are both hydrogen.

Suitable values for the substituent $R^1$ include allyl, dimethylallyl, butenyl, propargyl, benzyl, phenylethyl, phenylpropyl, furylmethyl, thienylmethyl, furylethyl, thienylethyl, imidazolylmethyl and pyridylmethyl; alternatively allyl, dimethylallyl, butenyl, propargyl, benzyl, phenylethyl, phenylpropyl, furylmethyl, thienylmethyl, imidazolylmethyl and pyridylmethyl, any of which groups may be optionally substituted by one or more substituents selected typically from halogen, cyano, trifluoromethyl, triazolyl, tetrazolyl, $C_{1-6}$ akyl-tetrazolyl, $C_{1-6}$ alkoxy, amino, di($C_{1-6}$)alkylamino, di($C_{1-6}$)alklaminomethyl, $C_{2-6}$ alkylcarbonylamino, $C_{2-6}$ alkoxycarbonylamino, N-($C_{1-6}$)alkyl-N-($C_{2-6}$)alkoxycarbonylamino, $C_{1-6}$ alkylsulphonylamino, aminocarbonylamino, aminocarbonyl, $C_{1-6}$ alkylaminocarbonyl, di($C_{1-6}$) alkylaminocarbonyl, aminosulphonyl, di($C_{1-6}$) alkylaminosulphonyl and $C_{1-6}$ alkylaminosulphonylmethyl.

Particular values of $R^1$ include allyl, dimethylallyl butenyl, propargyl, benzyl, fluorobenzyl, difluorobenzyl, cyanobenzyl, tetrazolyl-benzyl, methyltetrazolyl-benzyl methoxybenzyl, aminobenzyl, dimethylaminomethyl-benzyl, acetylamino-benzyl, aminocarbonyl-benzyl, methylaminocarbonyl-benzyl, dimethylaminocarbonyl-benzyl, aminosulphonyl-benzyl, dimethylaminosulphonyl-benzyl, trifluoromethyl-benzyl, phenylethyl, fluoro-phenylethyl, difluoro-phenylethyl, trifluoromethyl-phenylethyl, cyano-phenylethyl, methoxy-phenylethyl, triazolyl-phenylethyl, amino-phenylethyl, dimethylamino-phenylethyl, acetylamino-phenylethyl, methoxycarbonylamino-phenylethyl, (N-methyl-N-methoxycarbonyl)amino-phenylethyl, aminocarbonylamino-phenylethyl, fluoro(phenyl)propyl, phenylpropyl, furylmethyl, thienylmethyl furylethyl, thienylethyl, imidazolylmethyl, pyridylmethyl and amino-pyridylmethyl; other values are allyl, dimethylallyl, butenyl, propargyl benzyl, fluorobenzyl, difluorobenzyl, cyanobenzyl, tetrazolyl-benzyl, methyltetrazolyl-benzyl, methoxybenzyl, aminobenzyl dimethylaminomethyl-benzyl, acetylamino-benzyl, aminocarbonyl-benzyl, methylaminocarbonyl-benzyl, dimethylaminocarbonyl-benzyl, aminosulphonyl-benzyl, dimethylaminosulphonyl-benzyl, phenylethyl, fluoro-phenylethyl, difluoro-phenylethyl, trifluoromethyl-phenylethyl, cyano-phenylethyl, triazolyl-phenylethyl, amino-phenylethyl, dimethylamino-phenylethyl, acetylamino-phenylethyl methoxycarbonylamino-phenylethyl, (N-methyl-N-methoxycarbonyl)amino-phenylethyl, aminocarbonylamino-phenylethyl, phenylpropyl, furylmethyl, thienylmethyl imidazolylmethyl, pyridylm-ethyl and amino-pyridylmethyl.

Suitably, $R^2$ and $R^3$ independently represent hydrogen or methyl, especially hydrogen.

Suitably, $R^4$ represents hydrogen or methyl, especially hydrogen.

Suitably, $R^5$ and $R^6$ are independently selected from hydrogen, methyl, ethyl, n-propyl, isopropyl, n-butyl, t-butyl, trifluoromethyl phenyl, methylphenyl (especially 4-methylphenyl), benzyl and phenethyl.

In the compounds of formula I above, the substituent G suitably represents fluoro or methoxy.

Suitably, the substituent Z represents hydrogen, fluoro, cyano, hydroxy, methoxy, ethoxy, benzyloxy, methylamino-carbonyloxy, cyano-methoxy, aminocarbonyl-methoxy, methylsulphonyl, aminosulphonyl, N-methylamino-sulphonyl, N,N-dimethylamino-sulphonyl, amino, formylamino, acetylamino, trifluoromethyl-carbonylamino, benzyloxy-carbonylamino, methyl-sulphonylamino, ethyl-sulphonylamino, methylphenyl-sulphonylamino, N-methyl-(N-methylsulphonyl)-amino, N-methyl-(N-ethylsulphonyl)-amino, N-methyl-N-trifluoromethylsulphonyl)-amino, N-ethyl-(N-methylsulphonyl)-amino, N-benzyl-(N-methylsulphonyl)-amino, N-benzyl-(N-ethylsulphonyl)-amino, acetyl, methoxycarbonyl, ethoxycarbonyl aminocarbonyl, methylaminocarbonyl, ethylaminocarbonyl, propylaminocarbonyl, butylaminocarbonyl, benzylami-nocarbonyl or phenethyl-aminocarbonyl; or a group of for-mula (Za), (Zb), (Zc) or (Zd) as defined above; or an optionally substituted five-membered heteroaromatic ring as specified above.

In a particular embodiment, Z represents —SO$_2$NR$^5$R$^6$ in which $R^5$ and $R^6$ are as defined above. In a subset of this embodiment, $R^5$ and $R^6$ independently represent hydrogen or $C_{1-6}$ alkyl, especially hydrogen or methyl. Particular values of Z in this context include aminosulphonyl, N-methylamino-sulphonyl and N,N-dimethylamino-sulphonyl, especially N-methylamino-sulphonyl.

In another embodiment, Z represents a group of formula (Zb) in which $R^4$ is hydrogen or methyl. In a subset of this embodiment, X and Y both represent oxygen. In a particular aspect of this subset, the chiral centre denoted by the asterisk * is in the (S) configuration.

When the group Z represents an optionally substituted five-membered heteroaromatic ring, this is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, 1,2,4-oxadiazole, 1,2,4-thiadiazole or 1,2,4-triazole ring, in particular a 1,2,4-triazol-1-yl or 1,2,4-triazol-4-yl moiety.

Suitably, the five-membered heteroaromatic ring Z is unsubstituted. Examples of optional substituents which may typically be attached to the moiety Z include methyl, ethyl, benzyl and amino.

A particular sub-class of compounds according to the invention is represented by the compounds of formula IIA, and salts and prodrugs thereof:

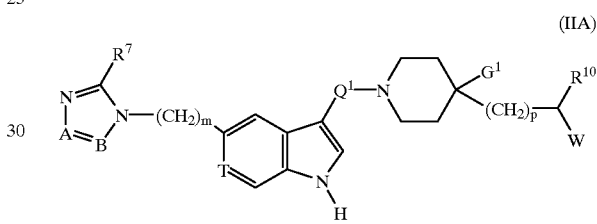

(IIA)

wherein m is zero, 1, 2 or 3, preferably zero or 1;

p is zero, 1 or 2;

$Q^1$ represents a straight or branched alkylene chain con-taining from 2 to 5 carbon atoms, optionally substituted in any position by one or more substituents selected from fluoro and hydroxy;

T represents nitrogen or CH;

$G^1$ represents fluoro or methoxy;

A represents nitrogen or CH;

B represents nitrogen or C-R$^8$;

$R^7$ and $R^8$ independently represent hydrogen, $C_{1-6}$ alkyl, $C_{2-6}$ alkenyl, $C_{3-7}$ cycloalkyl, aryl, aryl($C_{1-6}$)alkyl, $C_3$-heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$) alkylamino, halogen, cyano or trifluoromethyl;

W represents a group of formula (Wa), (Wb) or (Wc):

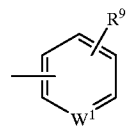

(Wa)

(Wb)

-continued

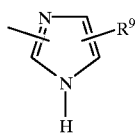
(Wc)

in which

W¹ represents CH or nitrogen;

W² represents oxygen, sulphur, NH or N-methyl;

R⁹ represents hydrogen, halogen, cyano, trifluoromethyl, triazolyl, tetrazolyl, $C_{1-6}$ alkyl-tetrazolyl, $C_{1-6}$ alkoxy, $C_{2-6}$ alkylcarbonyl, amino, $C_{1-6}$ alkylamino, di($C_{1-6}$)alkylamino, di($C_{1-6}$)alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl, di($C_{1-6}$) alkylaminosulphonyl or $C_{1-6}$ alkylaminosulphonylmethyl; and R¹⁰ represents hydrogen or $C_{1-3}$ alkyl optionally substituted by halogen.

Suitably, Q¹ represents a straight or branched 3 or 4 carbon allylene chain, optionally substituted in any position by one or more substituents selected from fluoro and hydroxy. Particular alkylene chains for Q¹ include propylene, butylene, 2-hydroxypropylene, 2-(hydroxymethyl)-propylene, 2-fluoropropylene and 2-(fluoromethyl)-propylene, especially propylene.

Particular values of R⁷ and R⁸ include hydrogen, methyl, ethyl, benzyl and amino, especially hydrogen.

Particular values of R⁹ include hydrogen, fluoro, cyano, triazolyl, tetrazolyl, methyl-tetrazolyl, methoxy, amino, dimethylaminomethyl, acetylamino, aminocarbonylamino, methylaminocarbonyl, aminosulphonyl and dimethylaminosulphonyl, especially hydrogen or fluoro.

Particular values of R¹⁰ include hydrogen and $C_{1-3}$ alkyl, for example hydrogen and methyl.

Another sub-class of compounds according to the invention is represented by the compounds of formula IIB, and salts and prodrugs thereof:

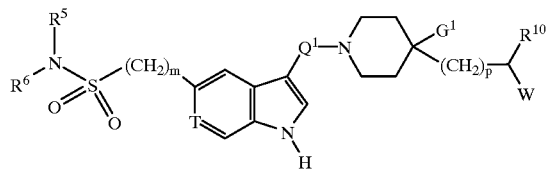
(IIB)

wherein m, p, Q¹, T, G¹, W and R¹⁰ are as defined with reference to formula IIA above; and R⁵ and R⁶ are as defined with reference to formula I above.

Particular values of R⁵ and R⁶ in relation to formula IIB above include hydrogen and $C_{1-6}$ alkyl, especially hydrogen or methyl. Suitably, one of R⁵ and R⁶ represents hydrogen and the other represents hydrogen or methyl.

A further sub-class of compounds according to the invention is represented by the compounds of formula IIC, and salts and prodrugs thereof:

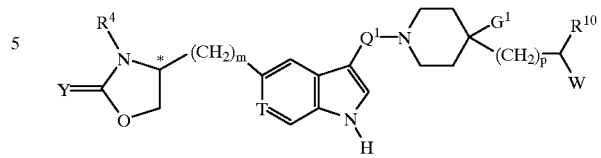
(IIC)

wherein the asterisk * denotes a chiral centre;

m, p, Q¹, T, G¹, W and R¹⁰ are as defined with reference to formula IIA above; and R⁴ and Y are as defined with reference to formula I above.

Particular values of R⁴ in relation to formula IIC include hydrogen and methyl.

Preferably, Y in formula IIC is oxygen.

Preferably, the chiral centre denoted by the asterisk * in formula IIC is in the (S) configuration.

Specific compounds within the scope of the present invention include:

4-benzyl-4-fluoro-1-[3-(5-(1,2,4triazol-4yl)-1H-indol-3-yl) propyl]piperidine;

4-fluoro-4-[2-(3-fluorophenyl)ethyl]-1-[3-(5-(1,2,4-triazol-4-yl)-1H-indol-3-yl)propyl]piperidine;

4-fluoro-4-(3-fluorobenzyl)-1-[3-(5-(1,2,4-triazol-4yl)-1H-indol-3-yl)propyl]piperidine;

4-fluoro-4-(2-fluorobenzyl)-1-[3-(5-(1,2,4-triazolyl)-1H-indol-3-yl)propyl]piperidine;

4-benzyl-4-methoxy-1-[3-(5-(1,2,4-triazol-4-yl)-1H-indol-3-yl)propyl]piperidine;

4-benzyl-4-methoxy-1-[3-(5-(1,2,4-triazol-1-ylmethyl)-1H-indol-3-yl)propyl]piperidine;

4-(2-fluorobenzyl)-4-methoxy-1-[3-(5-(1,2,4-triazol-4-yl)-1H-indol-3-yl)propyl]piperidine;

4-(3-fluorobenzyl)-4-methoxy-1-[3-(5-(1,2,4-triazol-4-yl)-1H-indol-3-yl)propyl]piperidine;

4-(4-fluorobenzyl)-4-methoxy-1-[3-(5-(1,2,4-triazol-4-yl)-1H-indol-3-yl)propyl]piperidine;

4-fluoro-4-[2-(trifluoromethyl)benzyl]-1-{3-[5-(1,2,4-triazol-4-yl)-1H-indol-3-yl]propyl}piperidine;

4-fluoro-4-[2-(N,N-dimethylaminosulfonyl)benzyl]-1-{3-[5-(1,2,4-triazol-4-yl)-1H-indol-3-yl]propyl}piperidine;

4-fluoro-4-(2-phenylpropyl)-1-{3-[5-(1,2,4-triazol-4-yl)-1H-indol-3-yl]propyl}piperidine;

4-fluoro-4-[3-fluoro-(2-phenyl)propyl]-1-{3-[5-(1,2,4triazol-4-yl)-1H-indol-3-yl]propyl}piperidine;

4-fluoro-4-[2-(4-fluorophenyl)ethyl]-1-{3-[5-(1,2,4-triazol-4-yl)-1H-indol-3-yl]propyl}piperidine;

4-fluoro-4-(2-phenylethyl)-1-{3-[5-(1,2,4-triazol-4-yl)-1H-indol-3-yl]propyl}piperidine;

4-fluoro-4-[2-(2-fluorophenyl)ethyl]-1-{3-[5-(1,2,4-triazol-4-yl)-1H-indol-3-yl]propyl}piperidine;

4-fluoro-4-[2-(2-methoxyphenyl)ethyl]-1-{3-[5-(1,2,4-triazol-4-yl)-1H-indol-3-yl]propyl}piperidine;

4-fluoro-4-[2-(2-thienyl)ethyl]-1-{3-[5-(1,2,4-triazol-4-yl)-1H-indol-3-yl]propyl}piperidine;

4-[2-(2-cyanophenyl)ethyl]-4-fluoro-1-{3-[5-(1,2,4-triazol-4-yl)-1H-indol-3-yl]propyl}piperidine;

4-fluoro-4-[2-(3-methoxyphenyl)ethyl]-1-{3-[5-(1,2,4-triazol-4-yl))-1H-indol-3-yl]propyl}piperidine;

4-fluoro-4-[2-(3-thienyl)ethyl]-1-{3-[5-(1,2,4-triazol-4-yl)-1H-indol-3-yl]propyl}piperidine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for admnistration orally or by injection include aqueous solutions, suitably flavoured syrups, aqueous or oil suspensions, and flavoured emulsions with edible oils such as cottonseed oil, sesame oil, coconut oil or peanut oil as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention wherein T represents CH, U represents $C-R^2$ and V represents $N-R^3$, corresponding to the indole derivatives of formula ID as defined above wherein T represents CH, may be prepared by a process which comprises reacting a compound of formula III:

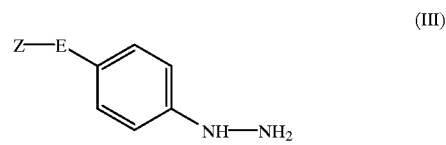

wherein Z and E are as defined above; with a compound of formula IV, or a carbonyl-protected form thereof:

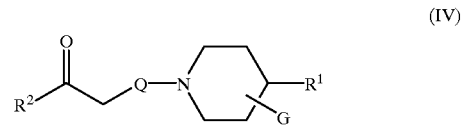

wherein Q, G, $R^1$ and $R^2$ are as defined above; followed, where required, by N-alkylation by standard methods to introduce the moiety $R^3$.

The reaction between compounds III and IV, which is an example of the well-known Fischer indole synthesis, is suitably carried out by heating the reagents together under mildly acidic conditions, e.g. 4% sulphuric acid at reflux.

Suitable carbonyl-protected forms of the compounds of formula IV include the dimethyl acetal or ketal derivatives. Where the alkylene chain Q contains a hydroxy group, this group may condense with the carbonyl moiety in compound IV, whereby the carbonyl moiety is protected in the form of a cyclic hemiacetal.

The Fischer reaction between compounds III and IV may be carried out in a single step, or may proceed via an initial non-cyclising step at a lower temperature to give an intermediate of formula V:

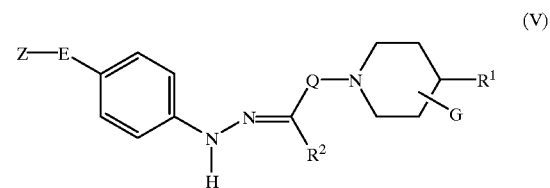

wherein Z, E, Q, G, $R^1$ and $R^2$ are as defined above; followed by cyclisation using a suitable reagent, e.g. a polyphosphate ester.

The intermediates of formula IV, or carbonyl-protected forms thereof, may be prepared by reacting a compound of formula VI, or a carbonyl-protected form thereof, with a compound of formula VII:

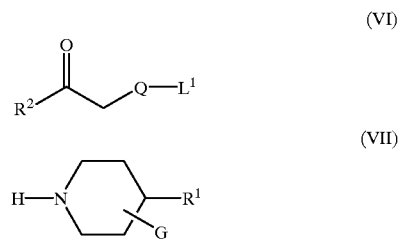

wherein Q, G, $R^1$ and $R^2$ are as defined above, and $L^1$ represents a suitable leaving group.

The leaving group $L^1$ is suitably a halogen atom, e.g. chlorine or bromine.

Where $L^1$ represents a halogen atom, the reaction between compounds VI and VII is conveniently effected by stiring the reactants under basic conditions in a suitable solvent, for example potassium carbonate in N,N-dimethylformamide, or triethylamine in tetrahydrofuran or acetonitrile.

In an alternative procedure, the compounds according to the invention may be prepared by a process which comprises reacting a compound of formula VII as defined above with a compound of formula VIII:

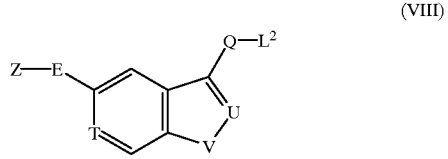
(VIII)

wherein Z, E, Q, T, U and V are as defined above, and $L^2$ represents a suitable leaving group.

The leaving group $L^2$ is suitably an alkylsulphonyloxy or arylsulphonyloxy group, e.g. methanesulphonyloxy (mesyloxy) or p-toluenesulphonyloxy (tosyloxy).

Where $L^2$ represents an alkylsulphonyloxy or arylsulphonyloxy group, the reaction between compounds VII and VIII is conveniently carried out in a suitable solvent such as 1,2-dimethoxyethane or isopropyl alcohol, typically in the presence of a base such as sodium carbonate or potassium carbonate, optionally with the addition of sodium iodide.

In one representative approach, the compounds of formula VIII wherein T and U both represent CH, V represents NH and $L^2$ represents a mesyloxy or tosyloxy group may be prepared by the sequence of steps illustrated in the following reaction scheme (cf. Larock and Yum, *J. Am. Chem. Soc.,* 1991, 113, 6689):

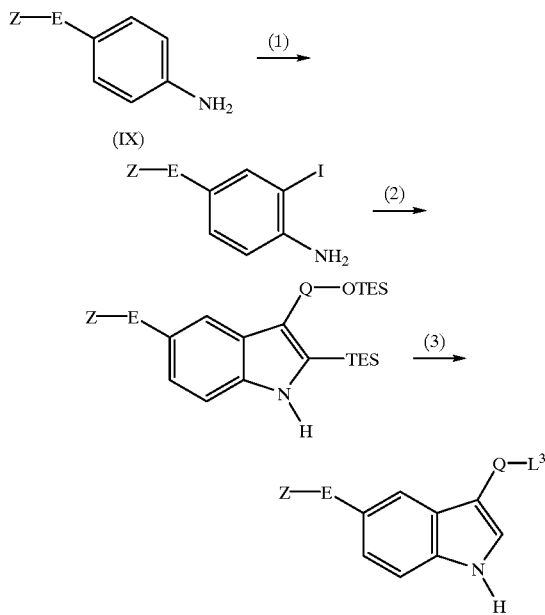

wherein Z, E and Q are as defined above, $L^3$ represents mesyloxy or tosyloxy, and TES is an abbreviation for triethylsilyl.

In Step 1 of the reaction scheme, the aniline derivative IX is treated with iodine monochloride, typically in methanol or acetonitrile, in order to introduce an iodine atom ortho to the amine moiety. Step 2 involves a palladium-mediated coupling reaction with the protected acetylene derivative TES-C≡-C-Q-OTES, typically using palladium acetate and -triphenylphosphine in the presence of lithium chloride and sodium carbonate, suitably in N,N-dimethylformamide at an elevated temperature. This is followed in Step 3 by removal of the TES moiety, typically by treatment with hydrochloric acid; followed in turn by mesylation or tosylation, suitably by using mesyl chloride or tosyl chloride respectively in the presence of a base such as triethylamine or pyridine, typically in dichloromethane/acetonitrile.

In another representative approach, the compounds of formula VIII wherein T and U both represent CH, V represents NIH, Q represents a propylene chain and $L^2$ represents a mesyloxy or tosyloxy group may be prepared by reacting 3,4dihydro-2H-pyran with a compound of formula III as defined above or a salt thereof, under a variant of the Fischer reaction conditions as described above for the reaction between compounds III and IV: followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by stirring the pyran derivative with an acid addition salt of the hydrazine derivative III, typically the hydrochloride salt, in an inert solvent such as aqueous ethanol. The resulting hydrazide derivative can then be cyclised by treatment with a Lewis acid such as zinc chloride, in a solvent such as 1,2-dimethoxyethane, suitably at the reflux temperature of the solvent.

In a further procedure, the compounds according to the invention wherein U represents nitrogen and V represents $N-R^3$, corresponding to the indazole derivatives of formula IB as defined above, may be prepared by a process which comprises cyclising a compound of formula X:

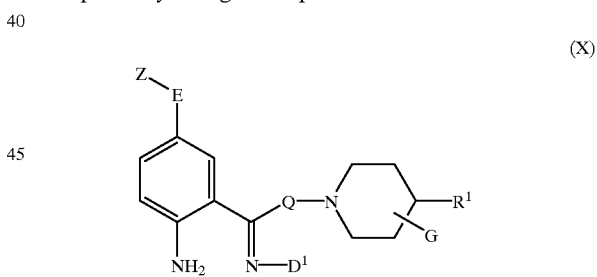
(X)

wherein Z, E, Q, G and $R^1$ are as defined above, and $D^1$ represents a readily displaceable group; followed, where required, by N-alkylation by standard methods to introduce the moiety $R^3$.

The cyclisation of compound X is conveniently achieved in a suitable organic solvent at an elevated temperature, for example in a mixture of m-xylene and 2,6-lutidine at a temperature in the region of 140° C.

The readily displaceable group $D^1$ in the compounds of formula X suitably represents a $C_{1-4}$ alkanoyloxy group, preferably acetoxy. Where $D^1$ represents acetoxy, the desired compound of formula X may be conveniently prepared by treating a carbonyl compound of formula XI:

(XI)

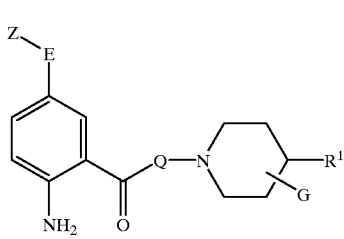

wherein Z, E, Q, G and R¹ are as defined above; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XI may conveniently be prepared by ozonolysis of the corresponding indole derivative of formula XII:

(XII)

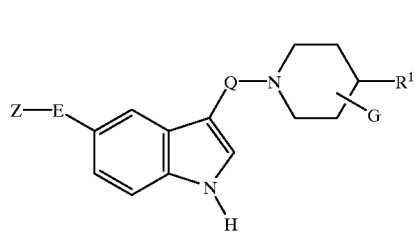

wherein Z, E, Q, G and R¹ are as defined above; followed by a reductive work-up, advantageously using dimethylsulphide.

The indole derivatives of formula XII may be prepared by methods analogous to those described in the accompanying Examples, or by procedures well known from the art.

In a still further procedure, the compounds according to the invention wherein T represents CH, U represents C-R² and V represents oxygen or sulphur, corresponding to the benzofuran or benzthiophene derivatives of formula IA wherein V is oxygen or sulphur respectively, may be prepared by a process which comprises cyclising a compound of formula XIII:

(XIII)

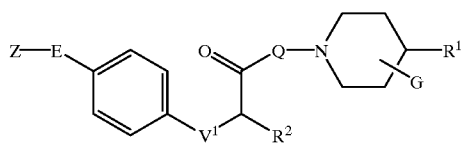

wherein Z, E, Q, G, R¹ and R² are as defined above, and V¹ represents oxygen or sulphur.

The cyclisation of compound XIII is conveniently effected by using polyphosphoric acid or a polyphosphate ester, advantageously at an elevated temperature.

The compounds of formula XIII may be prepared by reacting a compound of formula XIV with a compound of formula XV:

(XIV)

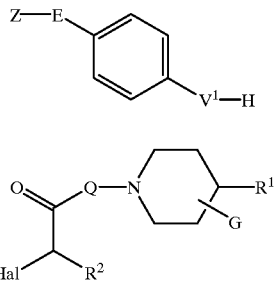

(XV)

wherein Z, E, Q, G, R¹, R² and V¹ are as defined above, and Hal represents a halogen atom.

The reaction is conveniently effected in the presence of a base such as sodium hydroxide.

The hydroxy and mercapto derivatives of formula XIV may be prepared by a variety of methods which will be readily apparent to those skilled in the art. One such method is described in EP-A-0497512.

In a yet further procedure, the compounds according to the invention may be prepared by a process which comprises reducing a compound of formula XVI:

(XV)

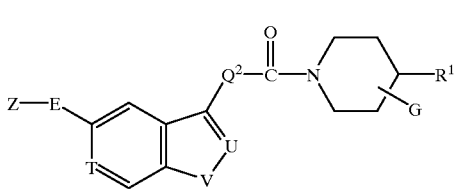

wherein Z, E, T, U, V, G and R¹ are as defined above, and —Q²—CH₂-corresponds to the moiety Q as defined above.

The reduction of compound XVI is conveniently effected by treating the appropriate compound with a reducing agent such as lithium aluminium hydride in an appropriate solvent, e.g. diethyl ether or tetrahydrofuran, or mixtures thereof.

The compounds of formula XVI above may suitably be prepared by reacting the appropriate compound of formula VII as defined above with a compound of formula XVII:

(XVII)

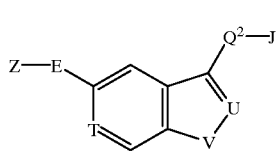

wherein Z, E, T, U, V and Q² are as defined above, and J represents a reactive carboxylate moiety.

Suitable values for the reactive carboxylate moiety J include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula XVII above wherein J is an acid chloride moiety may be prepared by treating the corresponding carboxylic acid derivative with thionyl chloride in toluene. Similarly, the intermediates of formula XVII wherein J is an acylimidazole moiety may be prepared by treating the corresponding carboxylic acid derivative with 1,1'-carbonyldiimidaaole. Alternatively, the reactive carboxylate moiety J may be obtained by treating the corresponding compound wherein J is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula VII.

The hydrazine derivatives of formula III above may be prepared by methods analogous to those described in EP-A-0438230, EP-A-0497512, EP-A-0548813 and WO-A-91/18897, as also may the aniline derivatives of formula IX.

Where they are not commercially available, the starting materials of formula VI, VII, XV and XVII may be prepared by methods analogous to those described in the accompanying Examples, or by standard procedures well known from the art.

It will be understood that any compound of formula I initially obtained from any of the above processes may, where appropriate, subsequently be elaborated into a further compound of formula I by techniques known from the art. For example a compound of formula I initially obtained wherein the $R^1$ moiety is substituted by nitro or cyano may be converted by catalytic hydrogenation to the corresponding amino- or aminomethyl-substituted compound respectively. Additionally, a compound of formula I wherein the $R^1$ moiety is substituted by hydroxy, possibly obtained by lithium aluminium hydride reduction of a precursor alkoxycarbonyl derivative, may be mesylated under standard conditions, and the mesyl group subsequently displaced by an amino moiety by treatment with the desired amine in a sealed tube at an elevated temperature. The amine derivative resulting from any of these procedures may then, for example, be N-acylated using the appropriate acyl halide, e.g. acetyl chloride; or aminocarbonylated, using potassium isocyanate, to the corresponding urea derivative; or converted to a 1,2,4-triazol-4-yl derivative using N,N-dimethylformamide azine; or reductively alkylated by treatment with the appropriate aldehyde or ketone in the presence of sodium cyanoborohydride. If desired, the amine derivative may also be carbamoylated by treatment with the requisite alkyl chloroformate. A compound of formula I initially obtained wherein the $R^1$ moiety is substituted by cyano may be converted, by treatment with sodium azide, to the corresponding tetrazole derivative, which in turn may be alkylated on the tetrazole ring by treatment with an alkyl halide under standard conditions. By way of additional illustration, a compound of formula I initially obtained wherein the $R^1$ moiety is substituted by an alkoxycarbonyl moiety may be saponified, by treatment with an alkali metal hydroxide, to the corresponding carboxy-substituted compound, which in turn may be converted to an amide derivative by treatment with the appropriate amine, advantageously in the presence of 1-(3-dimethylaminopropyl)-3-ethylcarbodiimide hydrochloride and 1-hydroxybenzotriazole. Moreover, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in N,N-dimethylformamide.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the $5\text{-HT}_{1D_\alpha}$ receptor subtype, inhibit forskolin-stimulated adenylyl cyclase activity, and stimulate [$^{35}$S]-GTPγS binding to membranes from clonal cell lines expressing human cloned receptors.

$5\text{-HT}_{1D_\alpha}/5\text{-HT}_{1D_\beta}$ Radioligand Binding

Chinese hamster ovary (CHO) clonal cell lines expressing the human $5\text{-HT}_{1D_\alpha}$ and $5\text{-HT}_{1D_\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, $CaCl_2$ 4; ascorbate 0.1%; pH 7.7 at room temperature) to give the required volume immediately prior to use (0.2 mg protein/ml). Incubations were carried out for 30 mm at 37° C. in the presence of 0.02–150 nM [$^3$H]-5-HT for saturation studies or 2–5 nM [$^3$H]-5-HT for displacement studies. The final assay volume was 1 ml. 5-HT (10 μM) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which $IC_{50}$ (the molar concentration of compound necessary to inhibit binding by 50%) values could be calculated for each test compound. The $IC_{50}$ values for binding to the $5\text{-HT}_{1D_\alpha}$ receptor subtype obtained for the compounds of the accompanying Examples were below 50 nM in each case. Furthermore, the compounds of the accompanying Examples were all found to possess a selective affinity for the $5\text{-HT}_{1D_\alpha}$ receptor subtype of at least 10-fold relative to the $5\text{-HT}_{1D_\beta}$ subtype.

$5\text{-HT}_{1D_\alpha}/5\text{-HT}_{1D_\beta}$ Adenylyl Cyclase Assay

Studies were performed essentially as described in *J. Pharmacol. Exp. Ther.*, 1986, 238, 248. CHO clonal cell lines expressing the human cloned $5\text{-HT}_{1D_\alpha}$ and $5\text{-HT}_{1D_\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of $\alpha$-[$^{33}$P]-ATP to [$^{33}$P]-cyclc AMP. A 10 $\mu$l aliquot of the membrane suspension was incubated, for 10–15 min, in a final volume of 50 $\mu$l, at 30° C., with or without forskolin (10 $\mu$M, in the presence or absence of test compound. The incubation buffer consisted of 50 mM Tris HCl (pH 7.6 at room temperature), 100 mM NaCl, 30 $\mu$M GTP, 50 $\mu$M cyclic AMP, 1 mM dithiothreitol, 1 mM ATP, 5 mM MgCl$_2$, 1 mM EGTA, 1 mM 3-isobutyl-1-methylxanthine, 3.5 mM creatinine phosphate, 0.2 mg/ml creatine phosphokinase, 0.5–1 $\mu$Ci $\alpha$-[$^{33}$P]-ATP and 1 nCi [$^3$H]-cyclic AMP. The incubation was initiated by the addition of membrane, following a 5 min preincubation at 30° C., and was terminated by the addition of 100 $\mu$l SDS (composition in mM: sodium lauryl sulphate 2%, ATP 45, cyclic AMP 1.3, pH 7.5 at room temperature). The ATP and cyclic AMP were separated on a double column chromatography system (Anal. Biochem., 1974, 58, 541). Functional parameters were determined using a least squares curve fitting programme ALLFIT (Am. J. Physiol., 1978, 235, E97) from which E$_{max}$ (maximal effect) and EC$_{50}$ (the molar concentration of compound necessary to inhibit the maximal effect by 50%) values were obtained for each test compound. Of those compounds which were tested in this assay, the EC$_{50}$ values for the $^5$-HT$_{1D_\alpha}$ receptor obtained for the compounds of the accompanying Examples were below 500 nM in each case. Moreover, the compounds of the accompanying Examples which were tested were all found to possess at least a 10-fold selectivity for the 5-HT$_{1D_\alpha}$ receptor subtype relative to the 5-HT$_{1D_\beta}$ subtype.

5-HT$_{1D_\alpha}$/5-HT$_{1D_\beta}$ GTP$\gamma$S Binding

Studies were performed essentially as described in Br. J. Pharmacol., 1993, 109, 1120. CHO clonal cell lines expressing the human cloned 5-HT$_{1D_\alpha}$ and 5-HT$_{1D_\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM, EDTA, pH 7.4 at room temperature and recentrifuged at 40,000 g, 4° C. for 15–25 minutes. The membranes were then resuspended in assay buffer (composition in mM: HEPES 20, NaCl 100, MgCl$_2$ 10, pargyline 0.01; ascorbate 0.1%; pH 7.4 at room temperature) at a concentration of 40 $\mu$g protein/ml for the 5-HT$_{1D_\alpha}$ receptor transfected cells and 40–50 $\mu$g protein/ml for the 5-HT$_{1D_\beta}$ receptor transfected cells. The membrane suspension was then incubated, in a volume of 1 ml, with GDP (100 $\mu$M for 5-HT$_{1D_\alpha}$ receptor transfected cells, 30 $\mu$M for the 5-HT$_{1D_\beta}$ receptor transfected cells) and test compound at 30° C. for 20 min and then transferred to ice for a further 15 min. [$^{35}$S]-GTP$\gamma$S was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which E$_{max}$ (maximal effect) and EC$_{50}$ (the molar concentration of compound necessary to inhibit the maximal effect by 50%) values were obtained for each test compound. Of those compounds which were tested in this assay, the EC$_{50}$ values for the 5-HT$_{1D_\alpha}$ receptor obtained for the compounds of the accompanying Examples were below 500 nM in each case. Moreover, the compounds of the accompanying Examples which were tested were all found to possess at least a 10-fold selectivity for the 5-HT$_{1D_\alpha}$ receptor subtype relative to the 5-HT$_{1D_\beta}$ subtype.

INTERMEDIATE 1

3-[5-(1,2,4-Triazol-4-yl)-1H-indol-3-yl]propan-1-ol 1. 4-Aminoacetanilide

A solution of 4-nitroacetanilide (5.0 g, 27.8 mmol) in EtOH/EtOAc (160 ml, 1:1), H$_2$O (15 ml) and 5N HCl (5.6 ml, 28.0 mmol) was hydrogenated over 10% Pd-C (0.50 g) at 50 psi for 0.25 h. The catalyst was removed by filtration through celite and the solvents removed under vacuum. The free base was generated by dissolving the product in H$_2$O, basifying with 2N NaOH and extracting into EtOAc. The combined extracts were dried (MgSO$_4$) and evaporated to give the title-aniline (3.75 g, 90%); $\delta_H$ (250 MHz, CDCl$_3$/d$_4$-MeOH) 2.10 (3H, s, Me), 6.68 (2H, d, J=8.8 Hz, Ar-H), 7.27 (2H, d, J=8.8 Hz, Ar-H).

2. 4-(1,2,4-Triazol-4-yl)acetanilide

A mixture of the preceding aniline (3.52 g, 23.4 mmol), N,N-dimethylformamide azine (3.33 g, 23.4 mmol; J. Chem. Soc. (C), 1967, 1664) and p-toluenesulphonic acid monohydrate (0.223 g, 1.17 mmol), in anhydrous toluene (100 ml) was heated at reflux for 17 h. The beige coloured precipitate was filtered off, washed with toluene and CH$_2$Cl$_2$, and dried under vacuum to give the desired triazole (4.29 g, 91%), $\delta_H$ (250 MHz, d$_4$-MeOH/d$_6$-DMSO) 2.14 (3H, s, CH$_3$), 7.60 (2H, d, J=8.8 Hz, Ar-H), 7.78 (2H, d, J=8.8 Hz, Ar-H), 8.96 (2H, s, Ar-H).

3. 4-(1,2,4-Triazol-4-yl)aniline

A solution of the preceding acetanilide (4.91 g, 24.3 mmol) in 5N HCl (100 ml) was heated at 125° C. for 1.5 h. The mixture was cooled to 0° C., basified with concentrated aqueous NaOH solution and extracted with CH$_2$Cl$_2$ (×5). The combined extracts were dried (MgSO$_4$) and evaporated and the residue chromatographed on silica gel, eluting with CH$_2$Cl$_2$/MeOH/NH$_3$ (80:8:1), to give the title-aniline (2.94 g, 76%); $\delta_H$ (250 MHz, CDCl$_3$) 3.80 (2H, s, NH$_2$), 6.71 (2H, d, J=8.8 Hz, Ar-H), 7.08 (2H, d, J=8.8 Hz, Ar-H:), 8.36 (2H, s, Ar-H).

4. 4-(1,2,4-Triazol-4-yl)phenylhydrazine

To a solution of the preceding aniline (1.60 g, 9.99 mmol) in concentrated HCl/H$_2$O (23 ml and 3 ml, respectively) was added, at −21° C., a solution of NaNO$_2$ (0.69 g, 9.99 mmol) in H$_2$O (8 ml), at such a rate as to maintain the temperature below −10° C. The mixture was stirred for 0.3 h and then filtered rapidly through a sinter, under vacuum. The filtrate was added to a cooled (−20° C.) solution of SnCl$_2$.2H$_2$O (9.02 g, 40.0 mmol) in concentrated HCl (17 ml). The mixture was stirred at −20° C. for 0.25 h and then at room temperature for 1.25 h. The resulting solid was filtered off, washed with Et$_2$O and dried under vacuum. The crude product was dissolved in H$_2$O, basified with concentrated aqueous NaOH and extracted with EtOAc (×5). The combined extracts were dried (MgSO$_4$) and evaporated to afford the title-product (0.95 g, 54%); $\delta_H$ (250 MHz, CDCl$_3$/d$_4$-MeOH) 3.98 (3H, br s, NH and NH$_2$), 6.97 (2H, d, J=12.0 Hz, Ar-H), 7.25 (2H, d, J=12.0 Hz, Ar-H), 8.48 (2H, s, Ar-H).

5. 3-[5-(1,2,4-Triazol-4-yl)-1H-indol-3-yl]propan-1-ol

A solution of 4-(1,2,4-triazol-4yl)phenylhydrazine (25 g, 143 mmol) in dioxan (250 ml) was treated with dihydropyran (24 g, 286 mmol) followed by 1M hydrochloric acid (150 ml) and heated at reflux for 18 h. The reaction mixture was evaporated, treated with toluene the re-evaporated. Inorganic solids were removed by treating the residue with a mixture of methanol and acetonitrile. The mother liquors were purified by column chromatography on silica using dichloromethane/methanol (9:1→4:1) as the eluant. The compound was recrystallised from acetonitrile to afford the title compound as a colourless solid (10.24 g, 30%); mp 205–207° C. (Found: C, 64.37; H, 5.76; N, 22.83. $C_{13}H_{14}N_4O$ requires: C, 64.45; H, 5.82; N, 23.13%.) $\delta_H$ (360 MHz, DMSO-$d_6$) 1.81 (2H, q, J=7 Hz, $CH_2$), 2.75 (2H, t, J=8 Hz, $CH_2$), 3.46 (2H, dt, $J_1$=6, $J_2$=5 Hz, $CH_2$), 4.43 (1H, t, J=5 Hz, OH), 7.26 (1H, d, J=2 Hz, Ar-H), 7.29 (1H, dd, $J_1$=9, $J_2$=2 Hz, Ar-H), 7.47 (1H, d, J=9 Hz, Ar-H), 7.77 (1H, d, J=2 Hz, Ar-H), 9.01 (2H, s, triazole-H), 11.05 (1H, br s, indole NH); m/z (CI) 243 ($M^+$+1)

INTERMEDIATE 2

6-Aza-6-tert-butyloxycarbonyl-1-oxaspiro[2.5]octane

Dimethyl sulphoxide (100 ml) was added dropwise to a stirred, cooled (10° C.) mixture of sodium hydride (3.70 g of a 55% oil dispersion, 0.0846 mol) and trimethylsulphoxonium iodide (18.6 g, 0.0846 mol) under a nitrogen atmosphere. After addition the cooling bath was removed and the mixture stirred at room temperature for 30 minutes, then cooled to 5° C. and was treated with a solution of N-tert-butyloxycarbonyl-4-piperidone (16.86 g, 0.0846 mol) in dimethylsulphoxide (50 ml). The cooling bath was removed and the reaction mixture stirred at room temperature for 15 minutes, then at 50° C. for 1 hour. The mixture was stirred whilst cooling to room temperature then quenched with water (40 ml) and stirred for a further 10 minutes. The reaction mixture was poured into water (600 ml) and extracted with toluene (4×300 ml). The combined organics were washed with water (300 ml), dried (sodium sulphate), then evaporated to give an oil which was eluted through a short silica column using ethyl acetate/n-hexane (1:1) to give a colourless solid (10.0 g, 55%), mp 49–51° C. (Found: C, 61.88; H, 9.05; N, 6.42. $C_{11}H_{19}NO_3$ requires C, 61.95; H, 8.98, N, 6.57%). $\delta_H$ (360 MHz, DMSO-$d_6$) 1.35–1.40 (2H, m. $CH_2$), 1.41 (9H, s, $C(CH_3)_3$), 1.60–1.67 (2H, m, $CH_2$), 2.65 (2H, s, $CH_2O$), 3.33–3.41 (2H, m, $CH_2$), 3.46–3.54 (2H, m, $CH_2$); m/z (ES) 214 ($M^+$+1).

INTERMEDIATE 3

3-[5-(1,2,4-Triazol-1-ylmethyl)-1H-indol-3-yl]propan-1-ol

The title compound was obtained from 2-iodo-4-(1,2,4-triazol-1-ylmethyl)aniline and 0,1-bis-triethylsilyl-1-pentyn-5-ol using the method described in Tet. Letts. 1994, 35, 6981–6984. mp 110–112° C., $\delta_H$ (360 MHz, DMSO-$d_6$) 1.79 (2H, qn, J=7 Hz, $CH_2CH_2CH2$), 2.70 (2H, t, J=7 Hz, indole-$CH_2$), 3.47 (2H, q, J=7 Hz, $CH_2OH$), 4.44 (1H, t, J=7 Hz, OH), 5.44 (2H, s, $CH_2$-triazole), 7.04 (1H, dd, J=8 and 1 Hz, Ar-H), 7.12 (1H, d, J=2 Hz, Ar-H), 7.30 (1H, d, J=8 Hz, Ar-H), 7.52 (1H, s, Ar-H), 7.94 (1H, s, triazole-H), 8.62 (1H, s, triazole-H), 10.80 (1H, s, indole-NH).

INTERMEDIATE 4

1-tert-Butyloxycarbonyl-4-ethynyl-4-fluoropiperidine 1. 1-tert-Butyloxycarbonyl-4-hydroxy-4-(2-trimethylsilylethynyl)-piperidine To a cooled (–40° C.) solution of trimethylsilylacetylene (34 ml 241 mmol) in anhydrous tetrahydrofuran (400 ml) under an atmosphere of nitrogen was added slowly n-butyl lithium (96 ml of a 2.5. M solution in hexanes, 241 mmol). After addition the mixture was stirred at –40° C. for 1 hour then cooled to –78° C. To this mixture was added via a cannula a solution of 1-tert-butyloxycarbonyl-4-piperidone (40 g, 201 mmol) in anhydrous tetrahydrofuran (250 ml). After addition the mixture was stirred at –78° C. for 1 hour, the cooling bath removed and the mixture stirred at room temperature for 72 hours. The reaction was quenched by the addition of saturated aqueous ammonium chloride (300 ml), stirred for a further 10 minutes and poured into water (500 ml) and extracted with ethyl acetate (3×300 ml). The combined organic solutions were washed with water (500 ml), brine (300 ml), dried ($MgSO_4$) and evaporated to afford the title compound (55 g, 92%); mp 75° C.; $\delta_H$ (250 MHz, $CDCl_3$) 0.19 (9H, s), 1.48 (9H, s), 1.63–1.74 (2H, m), 1.80–1.92 (2H, m), 3.18–3.28 (2H, m), 3.71–3.84 (2H, m); mlz (ES) 298 ($M^+$+1).

2. 1-tert-Butyloxycarbonyl-4-hydroxy-4-(2-trimethylsilylethynyl)-piperidine-cobalt hexacarbonyl To a solution of the product from the preceding step (55 g, 185 mmol) in diethyl ether (1000 ml) was added in a portionwise manner cobalt octacarbonyl (70 g, 203 mmol). After addition the mixture was stirred at room temperature for 4.5 hours then evaporated. The residue was purified by column chromatography (silica gel, hexane then diethyl ether-hexane 1:4) to give a red solid (80 g, 74%); $\delta_H$ (250 MHz, $CDCl_3$) 0.32 (9H, s), 1.48 (9H, s), 1.75 (4H, m), 3.14 (2H, m), 4.03 (2H, m).

3. 1-tert-Butyloxycarbonyl-4-ethynyl-4fluoropiperidine

To a cooled (–78° C.) and stirred solution of diethylaminosulfur trifluoride (18.1 ml, 137 mmol) in anhydrous dichloromethane (250 ml) was added via a cannula a solution of the product from the preceding step (80 g, 137 mmol) in anhydrous dichloromethane (400 ml) over 20 minutes, under nitrogen. After a further 1 hour at –78° C., the mixture was warmed to room temperature and stirred for a further 2 hours. Diethyl ether (1000 ml) was added and the organic solution was washed with a mixture of water (600 ml) and saturated aqueous potassium carbonate (300 ml), followed by brine (1×300 ml), dried ($MgSO_4$) and concentrated. The residue was dissolved in acetone (750 ml) and ceric ammonium nitrate (226 g, 412 mmol) added in 5 g portions over 1 hour. After addition the mixture was stirred at room temperature for a further 3 hours then evaporated. The residue was treated with water (500 ml) and the products extracted with dichloromethane (3×300 ml). The combined organic solutions were washed with water (1×400 ml), brine (1×200 ml), dried ($MgSO_4$) and concentrated. The residue was dissolved in anhydrous tetrahydrofuran (200 ml) cooled at 0° C. and tetrabutylammonium fluoride (137 ml of a 1.1M solution in THF, 151 mmol) added. After addition the mixture was stirred at 0° C. for 1 hour, then poured into water (500 ml) and products extracted with ethyl acetate (3×200 ml). The combined organic solutions were washed with water (1×400 ml), brine (1×200 ml), dried ($MgSO_4$) and concentrated. Flash chromatography of the residue (silica gel, diethyl ether-hexane 20:80) afforded 20 g (53%) of the required title compound, mp 45° C.; $\delta_H$ (360 MHz, $CDCl_3$) 1.46 (9H, s), 1.93–2.00 (4H, m), 2.70 (1H, d, J=5.0 Hz), 3.45–3.60 (4H, m).

EXAMPLE 1

4-Benzyl-4-fluoro-1-{3-[5-(1,2,4-triazol-4-yl)-1H-indol-3-yl]propyl}piperidine.2.1 Hydrogen Oxalate. 0.4 Hydrate a) 1-tert-Butyloxycarbonyl-4benzyl-4-hydroxypiperidine A solution of 4-benzyl-4-hydroxypiperidine (14.5 g, 75.8 mmol) in dichloromethane (150 ml) was treated portionwise with di-tert-butyl dicarbonate (16.55 g, 75.8 mmol) then stirred at ambient temperature for 4 hours. The solution was washed with 10% aqueous citric acid (50 ml), dried (sodium sulphate), then evaporated to afford a gum (23.8 g) which was purified by column chromatography on silica using ethyl acetate/petroleum ether (60–80) (1:1). The product was obtained (19.3 g, 87%) as a pale yellow solid, mp 87–88° C.; $\delta_H$ (360 MHz, DMSO-$d_6$) 1.32–1.37 (13H, m, $(CH_3)_3C$ and 2×$CH_2$), 2.67 (2H, s, $CH_2$Ph), 2.98–3.05 (2H, m, 2×CH), 3.63 (2H, d, J=12 Hz, 2×CH), 4.37 (1H, s, OH), 7.15–7.27 (5H, m, $C_6H_5$); m/z (ES) 292 ($M^+$+1).

b) 1-tert-Butyloxycarbonyl-4-benzyl-4fluoropiperidine

To a cooled (−71° C.) and stirred solution of diethylaminosulfur trifluoride (634 µl, 4.80 mmol) in anhydrous dichloromethane (15 ml) was added dropwise, via cannula, a solution of 1-tert-butyloxycarbonyl-4-benzyl-4-hydroxypiperidine (700 mg, 2.40 mmol) in anhydrous dichloromethane (15 ml) over 20 minutes, under nitrogen. After a further 50 minutes at −75° C., the mixture was warmed to −10° C. and stirred for a further 2 hours. Water (20 ml) and saturated aqueous potassium carbonate (7 ml) were added and products were extracted with diethyl ether (1×70 ml). The organic solution was washed with brine (1×25 ml), dried ($MgSO_4$) and concentrated. Flash chromatography of the residue (silica gel, hexane-diethyl ether, 86:14) gave 190 mg of 1-tert-butyloxycarbonyl-3,4-dehydro-4-benzylpiperidine and 360 mg (51%) of the title compound as pale yellow oils; $\delta_H$ (360 MHz, $CDCl_3$) 1.44 (9H, s), 1.46–1.78 (4H, m), 2.90 (2H, d, J=22 Hz), 2.98–3.08 (2H, m), 3.86–3.94 (2H, m), 7.16–7.34 (5H, m); m/z (ES) 294 ($M^+$1).

c) 4-Benzyl-4-fluoropiperidine

A solution of the product from the preceding step (360 mg) in a mixture of trifluoroacetic acid and dichloromethane (1:2; 12 ml) was allowed to stand at room temperature for 1 hour. Solvents were removed under vacuum and the residue was azeotroped with methanol (2×25 ml). Water (10 ml), 4N sodium hydroxide (5 ml) and brine (15 ml) were added and the product was extracted with ethyl acetate (2×50 ml). The combined organic solutions were dried ($Na_2SO_4$) and concentrated to give 235 mg (99%) of the title compound as a pale yellow oil which was used in the next step without further purification; OH (360 MHz, $CDCl_3$) 1.50–1.78 (4H, m), 2.84–2.96 (6H, m), 7.16–7.32 (5H, m); m/z (ES) 194 ($M^+$+1).

d) 4-Benzyl-4-fluoro-1-{3-[5-(1,2,4-triazol-4-yl)-1H-indol-3-yl]propyl}piperidine.2.1 Hydrogen Oxalate. 0.4 Hydrate To a stirred suspension of Intermediate 1 (206 mg, 0.85 mmol) in anhydrous tetrahydrofuran (35 ml) was added anhydrous triethylamine (237 ml, 1.70 mmol) followed by methanesulphonyl chloride (135 µl, 1.70 mmol) at room temperature, under nitrogen. After 1.5 hours of stirring, the mixture was diluted with ethyl acetate (100 ml), washed with brine (2×30 ml), dried ($MgSO_4$) and concentrated (bath temperature 35° C.). The remaining residue was dissolved in isopropanol (60 ml), potassium carbonate (164 mg, 1.19 mmol) and a solution of 4-benzyl-4-fluoropiperidine (230 mg, 1.19 mmol) in isopropanol (10 ml) were added, and the resulting mixture was refluxed for 18 hours, under nitrogen. The solvent was removed under vacuum, the residue was dissolved in water (50 ml) and saturated aqueous potassium carbonate (4 ml), and products were extracted with ethyl acetate (2×80 ml). The combined extracts were washed with brine (1×35 ml), dried ($Na_2SO_4$) and concentrated. Flash chromatography of the residue (silica gel dichloromethane-methanol-ammonia, 95:5:0.5) gave 164 mg (46%) of the title compound free base as a white foam. The oxalate salt was prepared from ethanol-diethyl ether, mp 79–85° C.

(Found: C, 57.15; H, 5.42; N, 11.24. $C_{25}H_{28}FN_5$×2.1 $(C_2H_2O_4)$×0.4$H_2O$ requires: C, 57.14; H, 5.42; N, 11.41%). $\delta_H$ (360 MHz, DMSO-$d_6$) 1.84–2.10 (6H, m), 2.76 (2H, t, J=7.2 Hz), 2.96–3.14 (6H, m), 3.32–3.42 (2H, m), 7.20–7.36 (7H, m), 7.51 (1H, d, J=8.5 Hz), 7.80 (1H, d, J=2.0 Hz), 9.01 (2H, s), 11.18 (1H, s); m/z (ES) 418 ($M^+$+1).

EXAMPLE 2

4-Fluoro-4-[2-(3-fluorophenyl)ethyl]-1-{3-[5-(1,2,4-triazol-4-yl)-1H-indol-3-yl]propyl}piperidine. 2.0 Hydrogen Oxalate a) 1-tert-Butyloxycarbonyl-4-[2-(3-fluorophenyl)ethyl]-4-hydroxypiperidine To magnesium turnings (494 mg), covered with anhydrous diethyl ether (3 ml), was added one crystal of iodine followed by a small amount (10%) of a solution of 3-fluorobenzyl bromide (4.12 g, 21.8 mmol) in anhydrous diethyl ether (8 ml). The mixture was warmed with a water bath (35° C.) to initiate Grignard formation, then the remaining solution of 3-fluorobenzyl bromide was added dropwise over 30 minutes at the same temperature. Steady refluxing was observed, which ceased after 30 minutes. The resulting mixture was cooled to −30° C. and a solution of Intermediate 2 (3.0 g, 14.07 mmol) in anhydrous diethyl ether (8 ml) was added dropwise over 20 minutes. A large amount of gelatinous precipitate was formed making sting difficult. The mixture was stirred at −10° C. for a further 4 hours 15 minutes, then quenched with saturated ammonium chloride (100 ml) and products were extracted with ethyl acetate (2×125 ml). The combined organic solutions were washed with brine (50 ml), dried ($MgSO_4$) and concentrated. Flash chromatography of the residue (silica gel, hexane-diethyl ether, 50:50 to 30:70) afforded 935 mg (20.5%) of the required title compound; $\delta_H$ (250 MHz, $CDCl_3$) 1.47 (9H, s), 1.54–1.64 (4H, m), 1.72–1.82 (2H, m), 2.66–2.78 (2H, m), 3.12–3.26 (2H, m), 3.78–3.90 (2H, m), 6.82–7.00 (3H, m), 7.18–7.30 (1H, m); m/z (ES) 324 ($M^+$+1).

b) 1-tert-Butyloxycarbonyl-4-fluoro-4-[2-(3-fluorophenyl)-ethyl]piperidine

To a cooled (−72° C.) and stirred solution of diethylaminosulfur trifluoride (760 µl, 5.75 mmol) in anhydrous dichloromethane (10 ml) was added dropwise, via cannula, a solution of the preceding alcohol (930 mg, 2.87 mmol) in anhydrous dichloromethane (15 ml) over 40 minutes, under nitrogen. After a further 50 minutes at −75° C., the mixture was warmed to −5° C. and stirred for 2 hours. Diethyl ether (100 ml) was added and the organic solution was washed with water-saturated aqueous potassium carbonate (2:1, 30 ml), brine (35 ml), dried ($MgSO_4$) and concentrated. Flash chromatography of the residue (silica gel, hexane-diethyl ether, 86:14) gave 500 mg of the title compound, impurified with 1-tert-butyloxycarbonyl-3,4-dehydro-4-[2-(3-fluorophenyl)ethyl]piperidine (ca 3:1). This was dissolved in dichloromethane (25 ml), m-chloroperoxy-benzoic acid (80–85%; 400 mg) was added, and the mixture was allowed to stand at room temperature for 12 hours. Diethyl ether (150 ml) was added and the solution was washed with 2N sodium hydroxide (25 ml).2N sodium hydroxide—10% aqueous sodium thiosulphite (1:1, 30 ml), dried ($MgSO_4$) and concentrated. Flash chromatography of the residue (silica gel, hexane-diethyl ether, 86:14) afforded 305 mg (33%) of the title compound as a colourless thick oil which solidified on standing; $\delta_H$ (250 MHz, $CDCl_3$) 1.47 (9H, s), 1.50–2.00 (6H, m), 2.68–2.78 (2H, m), 3.02–3.16 (2H, m), 3.90–4.00 (2H, m), 6.84–7.00 (3H, m), 7.18–7.30 (1H, m); m/z (ES) 326 ($M^+$+1).

c) 4-Fluoro-4-[2-(3-fluorophenyl)ethyl]piperidine

The title compound was prepared from the product of the preceding step following a similar method to that described for Example 1, step c. $\delta_H$ (250 MHz, CDCl$_3$-CD$_3$OD) 1.50–1.78 (2H, m), 1.82–2.00 (4H, m), 2.66–2.80 (2H, m), 2.88–3.00 (4H, m), 6.82–7.02 (3H, m), 7.18–7.30 (1H, m); m/z (ES) 226 (M$^+$+1).

d) 4-Fluoro-4-[2-(3-fluorophenyl)ethyl]-1-{3-[5-(1,2,4-triazol-4yl)-1H-indol-3-yl]propyl}piperidine.2.0 Hydrogen Oxalate The title compound free base was prepared from Intermediate 1 and the product from the preceding step following a silimar method to that described for Example 1, step d. The oxalate salt was prepared from ethanol-diethyl ether, mp 70–80° C. (Found: C, 57.06; H, 5.29; N, 11.17. C$_{26}$H$_{29}$F$_2$N$_5$×2.0C$_2$H$_2$O$_4$ requires: C, 57.23; H, 5.28; ,N, 11.12%). $\delta_H$ (360 MHz, DMSO-d$_6$) 1.86–2.14 (8H, m), 2.65–2.82 (4H, m), 3.00–3.20 (4H, m), 3.30–3.46 (2H, m), 6.96–7.12 (3H, m), 7.26–7.36 (3H, m), 7.50 (1H, d, J=8.6 Hz), 7.81 (1H, s), 9.02 (2H. s), 11.18 (1H, s); m/z (ES) 450 (M$^+$+1).

Examples 3 and 4 were prepared from 1-tert-butyloxycarbonyl-4-(3-fluorobenzyl)-4-hydroxypiperidine and 1-tert-butyloxycarbonyl-4-(2-fluorobenzyl)-4-hydroxypiperidine (see Example 7, step a) following a similar procedure to that described for Example 1 (steps b, c and d).

EXAMPLE 3

4-Fluoro-4-(3-fluorobenzyl)-1-{3-[5-(1,2,4-triazol-4-yl)-1H-indol-3-yl]proyl}piperidine. 1.5 Hydrogen Oxalate. 0.5 Etherate The oxalate salt was prepared from ethanol-diethyl ether, mp 80–83° C. (Found: C, 52.22; H, 5.00; N, 9.30. C$_{25}$H$_{27}$F$_2$N$_5$×1.5C$_2$H$_2$O$_4$×0.5C$_4$H$_{10}$O requires: C, 52.03; H, 5.03; N, 9.19%). $\delta_H$ (360 MHz, 9:1 CDCl$_3$ -DMSO-d$_6$) 1.86–1.97 (2H, m), 2.04–2.56 (4H, m), 2.87–2.98 (6H, m), 3.02–3.09 (2H, m), 3.40–3.50 (2H, m), 6.89–7.00 (3H, m), 7.13 (1H, dd, J=8 and 2 Hz), 7.22–7.33 (2H, m), 7.50 (1H, d, J=8 Hz), 7.55 (1H, d, J=2 Hz), 8.56 (2H, s) and 10.30 (1H, s); m/z (ES) 436 (M$^+$+1).

EXAMPLE 4

4-Fluoro-4-(2-fluorobenzyl)-1-{3-[5-(1,2,4-triazol-4-yl)-1H-indol-3-yl]propyl}piperidine. 1.0 Hydrogen Oxalate. 0.6 Hydrate The oxalate salt was prepared from ethanol-diethyl ether, mp 84–89° C. (Found: C, 55.75; H, 5.47; N, 11.22. C$_{25}$H$_{27}$F$_2$N$_5$×1.0C$_2$H$_2$O$_4$×0.6H$_2$O requires: C, 55.61; H, 5.18; N, 11.18%). $\delta_H$ (360 MHz, 9:1 CDCl$_3$-DMSO-d$_6$+CF$_3$CO$_2$H) 1.92–2.00 (2H, m), 2.25–2.56 (4H, m), 2.84–3.12 (8H, m), 3.40–3.50 (2H, m), 7.04–7.30 (6H, m), 7.51 (1H, d, J=8 Hz), 7.66 (1H, s) and 8.80 (2H, s); m/z (ES) 436 (M$^+$+1).

EXAMPLE 5

4-Benzyl-4-methoxy-1-{3-[5-(1,2,4-triazol-4-yl)-1H-indol-3-yl]propyl}piperidine. Hydrogen Oxalate.

a) 1-tert-Butyloxycarbonyl-4-benzyl-4-methoxypiperidine 1-tert-Butyloxycarbonyl-4-benzyl-4-hydroxypiperidine (Example 1, step a) (2.0 g, 6.87 mmol) was added to a stirred mixture of finely powdered potassium hydroxide (1.54 g, 27.5 mmol) in dimethyl sulphoxide (20 ml). After addition, the mixture was treated with iodomethane (0.85 ml, 13.7 mmol) then stirred at ambient temperature for 1 hour, poured into water (100 ml) and extracted with ethyl acetate (2×30 ml). The combined organics were washed with water (2×30 ml), dried (sodium sulphate) then evaporated to afford a gum (2.22 g) which was purified by column chromatography on silica using ethyl acetate/n-hexane (1:1). The title compound was obtained as a viscous colourless gum (1.23 g, 59%); $\delta_H$ (250 MHz, CDCl$_3$) 1.36–1.50 (2H, m, 2×CH), 1.43 (9H s, (CH$_3$)$_3$C), 1.62–1.77 (2H, m, 2×CH), 2.77 (2H, s, CH$_2$Ph), 2.95–3.06 (2H, m, 2×CH), 3.34 (3H, s, OCH$_3$), 3.70–3.90 (2H, m, 2×CH), 7.11–7.32 (5H, m, C$_6$H$_5$); m/z (ES) 306 (M$^+$+1).

b) 4-Benzyl-4-methoxypiperidine

The product from the preceding step (1.22 g, 4.0 mmol) and trifluoroacetic acid (3.1 ml 40 mmol) in dichloromethlie (20 ml) were stirred at ambient temperature for 24 hours. The solvent was evaporated and the residue partitioned between dichloromethane (30 ml) and saturated aqueous potassium carbonate solution (30 ml). The organic layer was separated then the aqueous re-extracted with dichloromethane (30 ml). The combined organics were dried (potassium carbonate) then evaporated to give a yellow gum (0.90 g) which was purified by column chromatography on silica using dichloromethane/methanol/ammonia (9:1:0.1). The title compound was obtained as a colourless viscous gum (0.80 g, 98%); $\delta_H$ (250 MHz, CDCl$_3$) 1.43–1.51 (2H, m, 2×CH), 1.68 (2H, d, J=12 Hz, 2×CH), 2.77 (2H, s, CH$_2$Ph), 2.78–2.92 (4H, m, 2×CH$_2$), 3.33 (3H, s, OCH$_3$), 7.14–7.30 (5H, m, C$_6$H$_5$); m/z (ES) 206 (M$^+$+1).

c) 4-Benzyl-4-methoxy-1-{3-[5-(1,2,4-triazol-4-yl)-1H-indol-3-yl]propyl}piperidine. Hydrogen Oxalate The title compound free base (135 mg, 29%) was obtained from the mesylate of 3-[5-(1,2,4-triazol-4-yl)-1H-indol-3-yl]propan-1-ol and 4benzyl-4-methoxypiperidine as described previously (Example 1, step d). The hydrogen oxalate salt had mp 110°–115° C. (Found: C, 61.99; H, 6.49; N. 12.09. C$_{26}$H$_{31}$N$_5$O×1.47C$_2$H$_2$O$_4$ requires; C, 61.86; H, 6.09; N, 12.46%). $\delta_H$ (360 MHz, DMSO-d$_6$) 1.65–1.74 (2H, m, 2×CH), 1.82 (2H, d, J=12 Hz, 2×CH, 1.98–2.06 (1H, m, CH$_2$CH$_2$CH$_2$), 2.76 (2H, t, J=7 Hz, indole-CH$_2$), 2.82 (2H, s, CH$_2$Ph), 2.82–3.00 (2H, m, 2×CH), 3.02–3.10 (2H,m, CH$_2$N), 3.20–3.32 (2H, m, 2×CH), 3.27 (3H, s, OCH$_3$), 7.18–7.34 (7H, m, indole-H, C$_6$H$_5$, Ar-H), 7.50 (1H, d, J=8 Hz, Ar-H), 7.79 (1H, d, J=2 Hz, Ar-H), 9.01 (2H, s, triazole-H), 11.18 (1H, s, indole-NH), m/z (ES) 430 (M$^+$+1).

EXAMPLE 6

4-Benzyl-4-methoxy-1-(3-[5-(1,2,4-triazol-1-ylmethyl)-1H-indol-3-yl]-propyl)piperidine Hydrogen Oxalate A stirred, cooled (−5° C.) solution of 3-(5-[1,2,4-triazol-1-ylmethyl)-1H-indol-3-yl)propan-1-ol (260 mg, 1 mmol) in anhydrous tetrahydrofuran (20 ml), under a nitrogen atmosphere, was treated with triethylamine (0.17 ml, 1.2 mmol) and methanesulphonyl chloride (0.10 ml, 1.2 mmol). After 45 minutes the reaction mixture was filtered, then washed through the filter pad with tetrahydrofuran (10 ml). The resulting mesylate solution was treated with potssium carbonate (263 mg, 1.9 mmol), sodium iodide (285 mg, 1.9 mmol) and a solution of 4-benzyl-4-methoxypiperidine (400 mg, 1.9 mmol) in tetrahydrofuran (10 ml). The reaction mixture was stirred whilst heating at 50° C. for 24 hours. The solvent was evaporated, the residue partitioned between dichloromethane (40 ml) and water (20 ml). The organic layer was separated and the aqueous re-extracted with dichloromethane (40 ml). The combined organics were extracted with aqueous citric acid (1 g in 20 ml), the aqueous was basified to pH=12 with 40% aqueous soldium hydroxide then extracted with dichloromethane (3×30 ml). The organic extracts were combined, dried (potassium carbonate) then evaporated. The residue was purified by column chromatography on silica using dichloromethane/methanol/ammonia (9:1:0.1) to afford the title compound free base as a glass (332 mg, 75%). The hydrogen oxalate salt has mp 84°–87° C. (Found: C, 60.81: H. 6.34: N, 11.68. $C_{27}H_{33}N_5O$. $1.75C_2H_2O_4$ requires C, 60.94; H, 6.12; N, 11.65%). $\delta_H$ (360 MHz, DMSO-$d_6$) 1.6–5–1.78 (2H, m, 2×CH), 1.82 (2H, d, J=12 Hz, 2×CH), 1.94–2.04 (2H, m, $CH_2CH_2CH_2$), 2.71 (2H, t, J=7 Hz, indole-$CH_2$), 2.82 (2H, s, $CH_2$Ph), 2.82–3.00 (2H, m, 2×CH), 3.02–3.12 (2H, m, $CH_2$N), 3.22–3.32 (2H, m, 2×CH), 3.28 (3H, s, $OCH_3$) 5.43 (2H, s, $CH_2$-triazole), 7.05 (1H, d, J=7 Hz, Ar-H), 7.18–7.34 (7H, m, $C_6H_5$, indole-H, Ar-H), 7.52 (1H, s, Ar-H), 7.94 (1H, s, triazole-H), 8.60 (1H, s, triazole-H), 10.92 (1H, s, indole-NH); m/z (ES) 444 ($M^+$+1).

EXAMPLE 7

4-(2-Fluorobenzyl)-4methoxy-1-(3-[5-(1,2,4-triazol-4-yl)-1H-indol-3-yl]propyl)piperidine Hydrogen Oxalate a) 1-tert-Butyloxycarbonyl-4-(2-fluorobenzyl)-4-hydroxypiperidine 1-Benzyl-4-piperidone (10 g, 53 mmol) in diethyl ether (80 ml) was added dropwise to a cooled (−4° C.), stirred mixture of 2-fluorobenzyl magnesium bromide (prepared from magnesium and 2-fluorobenzyl bromide (9.56 ml, 80 mmol) in diethyl ether (65 ml)) under an atmosphere of nitrogen. The reaction mixture was stirred whilst warming to room temperature (30 minutes) then at room temperature for 20 minutes. The reaction mixture was quenched with 2M hydrochloric acid (100 ml). The aqueous was separated and washed with diethyl ether (100 ml). The aqueous was basified with 2M sodium hydroxide solution then exhaustively extracted with dichloromethane. The combined organics were dried (sodium sulphate) then evaporated to give crude 1-benzyl-4-(2-fluorobenzyl)-4-hydroxypiperidine as a gum (9.0 g). This crude product in methanol (100 ml) was treated with formic acid (6 ml), ammonium formate (9.5 g, 0.15 mol) and 10% palladium on carbon (900 mg). The mixture was stirred whilst heating at reflux for 4 hours, cooled, filtered then evaporated to afford 4-(2-fluorobenzyl)-4-hydroxypiperidine as a gum (3.4 g); m/z (ES) 210 ($M^+$+1). This amine (3.35 g, 16 mmol) in dichloromethane (75 ml) was treated with di-t-butyldicarbonate (3.5 g, 16 mmol) and stirred at ambient temperature for 18 hours, washed with aqueous 10% citric acid, dried (potassium carbonate), evaporated to give a gum which was purified by column chromatography on silica using ethyl acetate/n-hexane (1:1) to afford the title compound as a colourless, viscous gum (3.62 g, 73%). $\delta_H$ (360 MHz, $CDCl_3$) 1.46 (9H, s, $(CH_3)_3$C), 1.48 (2H, d, J=13 Hz, 2×CH), 1.63 (2H, ddd, $J_1$=5, $J_2$=13, $J_3$=17 Hz, 2×CH), 2.82 (2H, d, J=1 Hz, $CH_2$Ph), 3.11 (2H, ddd, $J_1$=3, $J_2$=$J_3$=13 Hz, 2×CH), 3.84 (2H, d, J=13 Hz, 2×CH), 7.02–7.27 (4H, m, $C_6H_4$); m/z (ES) 310 ($M^+$+1).

b) 1-tert-Butyloxycarbonyl-4-(2-fluorobenzyl)-4-methoxypiperidine

The title compound was obtained (320 mg, 31%) from the product of the preceding step as described for Example 5 (step a); $\delta_H$ (360 MHz, DMSO-$d_6$) 1.30–1.34 (2H, m, 2×CH), 1.36 (9H, s), $(CH_3)_3$C), 1.60–1.64 (2H, m, 2×CH), 2.80 (2H, s, $CH_2$Ph), 2.82–2.98 (2H, m, 2×CH), 3.25 (3H, s, $OCH_3$), 3.65–3.68 (2H, m, 2×CH), 7.10–7.28 (4H, m, $C_6H_4$); m/z (ES) 324 ($M^+$+1).

c) 4-(2-Fluorobenzyl)-4-methoxypiperidine

The title compound was obtained (181 mg, 82%) from the product of the preceding step as described for Example 5 (step b); $\delta_H$ (250MHz, DMSO-$d_6$) 1.37–1.49 (2H, m, 2×CH), 1.64–1.68 (2H, m, 2×CH), 2.65–2.75 (4H, m, 2×$CH_2$), 2.87 (2H, s, $CH_2$Ph), 3.34 (3H, s, $OCH_3$), 7.21–7.43 (4H, m, $C_6H_4$); m/z (ES) 224 ($M^+$+1).

d) 4-(2-Fluorobenzyl)-4-methoxy-1-{3-[5-(1,2,4-triazol-4-yl)-1H-indol-3-yl]propyl}piperidine Hydrogen Oxalate The title compound free base was obtained (105 mg, 33%) from the mesylate of 3-[5-(1,2,4-triazol-4-yl)-1H-indol-3-yl]propan-1-ol and 4-(2-fluorobenzyl)-4-methoxypiperidine as described previously. The hydrogen oxalate salt had mp 110°–115° C. (Found: C. 56.94; H, 5.80; N. 11.04. $C_{26}H_{30}FN_5O.2.1C_2H_2O_4$ requires: C, 56.98; H, 5.42; N, 11.00%). $\delta_H$ (360 MHz, DMSO-$d_6$) 1.64–1.78 (2H, m, 2×CH), 1.80–188 (2H, m, 2×CH), 1.96–2.04 (2H, m, $CH_2CH_2CH_2$), 2.70–2.78 (2H, m, indole-$CH_2$), 2.84 (2H, s, CHPh), 2.90–2.98 (2H, m, 2×CH), 3.02–3.10 (2H, m, $CH_2$N), 3.26 (3H, s, $OCH_3$), 3.25–3.32 (2H, m, 2×CH), 7.13–7.33 (6H, m, $C_6H_4$, Ar-H, indole-H), 7.49 (1H, d, J=8 Hz, Ar-H), 7.89 (1H, s, Ar-H), 9.00 (2H, s, 2 × triazole-H), 11.18 (1H, s, indole-NH); m/z (ES) 448 ($M^+$+1).

EXAMPLE 8

4-(3-Fluorobenzyl)-4-methoxy-1-{3-[5-(1,2,4-triazol-4-yl)-1H-indol-3-yl]propyl}piperidine Hydrogen Oxalate The title compound free base was obtained (85 mg, 44%) from the mesylate of 3-[5-(1,2,4-triazol-4-yl)-1H-indol-3-yl]propan-1-ol and 4-(3-fluorobenzyl)-4-methoxypiperidine as described previously. The hydrogen oxalate salt had mp>105° C. (Found: C, 57.81; H, 5.95; N, 11.05%. $C_{26}H_{30}FN_5O$. $1.85C_2H_2O_4$ requires: C, 58.09; H, 5.53; N, 11.40%); m/z (ES) 448 ($M^+$+1).

EXAMPLE 9

4-(4-Fluorobenzyl)-4-methoxy-1-{3-[5-(1,2,4-triazol-4-yl)-1H-indol-3-yl]propyl}-piperidine Hydrogen Oxalate The title compound free base was obtained (50 mg, 20%) from the mesylate of 3-(5-(1,2,4-triazol-4-yl)-1H-indol-3-yl]propan-1-ol and 4-(4-fluorobenzyl)-4-methoxypiperidine as described previously. The hydrogen oxalate salt had mp>95° C. (dec.). (Found: C, 58.77; H, 5.89; N. 11.53. $C_{26}H_{30}FN_5O$. $1.75C_2H_2O_4$ requires: C, 58.55; H. 5.58; N. 11.57%); m/z (ES) 448 ($M^+$+1).

EXAMPLE 10

4-Fluoro-4-[2-(trifluoromethyl)benzyl]-1-{3-[5-(1,2,4-triazolivy-1H-indol-3-yl]propyl}piperidine. 2.0 Hydrogen Oxalate. 0.4 Etherate. 0.25 Hydrate a) 1-tert-Butyloxycarbonyl-4-[2-(trifluoromethyl)benzyl]-4-hydroxypiperidine 2-Bromobenzotrifluoride (0.70 ml, 5.1 mmol) was added dropwise at −78° C. to a stirred solution of tert-butyllithium (1.7 M in pentane, 6.0 ml) in anhydrous diethyl ether (25 ml) under nitrogen. After 30 minutes, a solution of Intermediate 2 (1.0 g, 4.69 mmol) was added. The white suspension was stirred at −78° C. for 1.5 hours, then warmed slowly to room temperature and stirred for a further 18 hours. The mixture was diluted with saturated aqueous ammonium chloride (100 ml) and extracted with diethyl ether (2×50 ml). The extracts were dried ($MgSO_4$), filtered and concentrated. Flash column chromatography on silica, eluting with 30% then 50% ethyl acetate-hexane, gave the product (1.44 g, 86%) as a pale yellow glass; $\delta_H$ (360 MHz, $CDCl_3$) 1.45 (9 H, s), 1.49 (2 H, dd, J=13 and 2), 1.65 (2 H, ddd, J=13, 13 and 5), 2.99 (2 H, s), 3.05 (2 H, ddd, J=13, 13 and 3), 3.90 (2 H, broad d, J=13), 7.35 (1 H, dd, J=7 and 7), 7.47–7.55 (2 H, m) and 7.67 (1 H, d, J=8); m/z (ES) 360 ($M^+$+1).

b) 1-tert-Butyloxycarbonyl-4-[2-(trifluoromethyl)benzyl]-4-fluoropiperidine

The title compounud (0.70 g, 49%) was prepared from the product of the preceding step (1.43 g, 3.98 mmol) following a similar method to that described for Example 2, step b. $\delta_H$ (360 MHz, CDCl$_3$) 1.46 (9 H, s), 1.55–1.68 (4 H, m), 2.92–3.03 (2 H, m), 3.13 (2 H, d, J=24), 3.88–4.04 (2 H, m), 7.35 (1 H, dd, J=8 and 8), 7.49 (1H, d, J=8 and 8), 7.57 (1 H. d, J=8) and 7.65 (1 H, d, J=8); m/z (ES) 384 [M$^+$+23 (Na)].

c) 4-[2-Trifluoromethyl)benzyl]-4-fluoropiperidine

The title compound (0.454 g, 92%) was prepared from the product of the preceding step (0.687 g, 1.90 mmol) following a similar method to that described for Example 1, step c. $\delta_H$ (250 NHz, CDCl$_3$) 1.50–1.75 (4 H, m)2.81–2.94 (4 H, m), 3.13 (2 H, a, J=24), 7.34 (1 H, dd, J=8 and 8), 7.49 (1 H, dd, J=8 and 8), 7.58 (1 H, d, J=8) and 7.65 (1 H, d, J=8); m/z (ES) 262 (M$^+$+1).

d) 4-Fluoro-4-[2-(trifluoromethyl)benzyl]-1-{3-[5-(1,2,4-triazol-4-yl)-1H-indol-3-yl]propyl}piperidine. 2.0 Hydrogen Oxalate. 0.4 Etherate. 0.25 Hydrate The title compound free base (0.133 g, 29%) was prepared from Intermediate 1 and the product of the preceding step following a similar method to that described for Example 1, step d. The oxalate salt was prepared from ethanol-diethyl ether, m.p. 88–91° C. (Found: C, 54.24; H, 4.90; N, 9.76. C$_{26}$H$_{27}$N$_5$F$_4$×2.0C$_2$H$_2$O$_4$×0.4C$_4$H$_{10}$O× 0.25H$_2$O requires C, 54.24; H, 5.11; N, 10.01%.) $\delta_H$ (360 MHz, 9:1 CDCl$_3$+d$_6$-DMSO) 1.58–1.66 (2 H. m), 1.90–2.10 (4 H, m), 2.54–2.60 (2 H, m), 2.65–2.78 (2 H, m), 2.80–2.87 (2 H, m), 2.91 (2 H, d, J=24), 3.18–3.24 (2 H, m), 6.86 (1 H, dd. J=9 and 1), 6.92 (1 H, s), 7.13 (1 H, dd, J=8 and 8), 7.21–7.27 (4 H. m), 7.38 (1 H, d, J=8), 8.30 (2 H, s) and 10.25 (1 H, s); m/z (ES) 486 (M$^+$+1).

EXAMPLE 11

4-Fluoro-4-[2-(N,N-dimethylaminosulfonyl)benzyl]-1-{3-[5-(1,2,4-triazol-4-yl)-1H-indol-3-yl]propyl}piperidine. 2.0 Hydrogen Oxalate. 0.2 Etherate. 0.5 Hydrate Example 11 was prepared from N,N-dimethylbenzenesulfonamide following a similar procedure to that described for Example 10 (steps a, b, c and d).

The oxalate salt was prepared from ethanol-diethyl ether, m.p. 94–98° C. (Found: C, 52.49; H, 5.41; N. 11.48. C$_{27}$H$_{33}$N$_6$SO$_2$F×2.0C$_2$H$_2$O$_4$× 0.2C$_4$H$_{10}$O×0.5H$_2$O requires C, 52.43; H, 5.53; N, 11.54%.) $\delta_H$ (360 MHz, d$_6$-DMSO) 1.76–1.86 (2 H, m), 1.90–2.15 (4 H, m), 2.68 (6 H, s), 2.72–2.80 (2 H, m), 2.92–3.05 (2 H, m), 3.06–3.14 (2 H, m), 3.36–3.44 (2 H, m), 3.46 (2 H, d, J=25), 7.31–7.33 (2 H, m), 7.49–7.56 (3 H, m), 7.67 (1 H, dd, J=7), 7.79–7.81 (2 H, m), 9.00 (2 H, s) and 11.18 (1 H, s);mlz (ES) 525 (M$^+$+1).

EXAMPLE 12

4-Fluoro-4-(2-phenylpropyl)-1-{3-[5-(1,2,4-triazol-4yl)-1H-indol-3-yl]propyl}piperidine. 2.0 Hydrogen Oxalate. 0.15 Etherate. 0.05 Hydrate a) 1-tert-Butyloxycarbonyl-4-[(2-phenyl)allyl]-4-hydroxypiperidine A solution of tert-butyllithium in pentane (1.7 M, 11 ml) was added dropwise at −78° C. to a stirred solution of a-bromostyrene (2.3 ml, 17.7 mmol) in anhydrous THF (80 ml) under nitrogen. After 20 minutes, a solution of Intermediate 2 (2.0 g, 9.38 mmol) in anhydrous THF (6 ml) was added. The black solution was warmed slowly to room temperature over 7 hours. The mixture was diluted with saturated aqueous ammonium -chloride (200 ml) and extracted with ethyl acetate (100 ml). The extract was washed with brine (50 ml), dried (MgSO$_4$), filtered and concentrated. Flash column chromatography on silica, eluting with 20% then 60% ethyl acetate-hexane, gave the title compound (1.67 g, 56%) as a yellow oil. $\delta_H$ (360 MHz, CDCl$_3$) 1.39–1.47 (13 H, m), 1.57 (1 H, s), 2.74 (2 H, s), 2.98–3.10 (2 H, m), 3.70–4.02 (2 H, m) and 7.26–7.42 (5 H, m); m/z (ES) 318 (M$^+$+1).

b) 1-tert-Butyloxycarbonyl-4-(2-phenylpropyl)-4-hydroxypiperidine

A solution of 1-tert-butyloxycarbonyl-4-[(2-phenyl)allyl] 4-hydroxypiperidine (1.67 g, 5.26 mmol) in ethyl acetate (25 ml) was hydrogenated over 1% palladium on activated carbon (0.8 g) at room temperature and 1 atm pressure of hydrogen for 1.5 hours. The mixture was filtered and the filtrate was concentrated to yield the title compound (1.47 g, 87%) as a pale yellow glass. $\delta_H$ (250 MHz, CDCl$_3$) 1.27 (3 H, d, J=7), 1.36–1.60 (13 H, m), 1.73 (1 H, dd, J=15 and 4), 2.01 (1 H, dd, J=15 and 10), 2.98–3.06 (3 H, m), 3.60–3.88 (2 H, m) and 7.16–7.36 (5 H, m); m/z (ES) 320 (M$^+$+1).

c) 1-tert-Butyloxycarbonyl-4-(2-phenylpropyl)-4-fluoropiperidine

The title compound (0.651 g, 44%) was prepared from the product of the preceding step (1.47 g, 4.60 mmol) following a similar method to that described for Example 2, step b. $\delta_H$ (250 MHz, CDCl$_3$) 1.28 (3 H, d, J=7), 1.43 (9 H, s), 1.47–2.11 (6 H, m), 2.93–3.07 (3 H, m), 3.76–3.86 (2 H, m) and 7.15–7.33 (5 H, m); m/z (ES) 322 (M$^+$+1).

d) 4-(2-Phenylpropyl)-4-fluoropiperidine

The title compound (0.374 g, 85%) was prepared from the product of the preceding step (0.640 g, 1.99 mmol) following a similar method to that described for Example 1, step c. $\delta_H$ (360 MHz, CDCl$_3$) 1.28 (3 H, d, J=7), 1.35–1.60 (2 H, m), 1.70–1.79 (2 H, m), 1.83–2.09 (2 H, m), 2.79–2.93 (4 H, m), 3.03 (1 H, qt, J=7 and 7), 7.15–7.22 (3 H, m) and 7.26–7.31 (2 H, m); m/z (ES) 222 (M$^+$+1).

e) 4-Fluoro-4-(2-phenylpropyl)-1-{3-[5-(1,2,4-triazol-4-yl)-1H-indol-3-yl]propyl}piperidine. 2.0 Hydrogen Oxalate. 0.15 Etherate. 0.05 Hydrate The title compound free base (0.119 g, 32%) was prepared from Intermediate 1 and the product of the preceding step following a similar method to that described for Example 1, step d. The oxalate salt was prepared from ethanol-diethyl ether, m.p. 87–91° C. (Found C, 59.24; H, 5.95; N, 11.28. C$_{27}$H$_{32}$N$_5$F×2.0C$_2$H$_2$O$_4$×0.15C$_4$H$_{10}$O×0.05H$_2$O requires C, 59.52; H, 5.94; N, 10.98%.) $\delta_H$ (360 MHz, d$_6$-DMSO) 1.21 (3 H. d, J=7), 1.60–2.10 (10 H, m), 2.75 ( 2 H, t, J=8), 2.90–3.12 (4 H, m), 3.26–3.28 (1 H, m), 7.16–7.20 (1 H, m), 7.24–7.35 (6 H, m), 7.50 (I H, d, J=9), 7.79 (1 H, s), 9.01 (2 H, s) and 11.17 (1 H, s); m/z (ES) 446 (M$^+$+1).

EXAMPLE 13

4-Fluoro-4-[3-fluoro-(2-phenyl)propyl]-1-{3-[5-(1,2,4-triazol-4-yl)-1H-indol-3-yl]-propyl}piperidine a) 3-(1-tert-Butyloxycarbonyl-4-hydroxypiperidin-4-yl)-2-phenylpropionic acid methyl ester A solution of lithium hexamethyldisilylamide (1 M, 22 ml) in THF was diluted with dry THF (40 ml) and stirred at −70° C. under nitrogen. Methyl 2-phenylacetate (3.00 ml, 20.9 mmmol) was added dropwise and the orange solution was stirred for 30 minutes. A solution of Intermediate 2 (4.26 g, 20 mmol) in dry THF (12 ml) was added, followed by dropwise addition of boron trifluoride etherate (2.5 ml, 20.3 mmol). The mixture was stirred at −70 ° C. for 1.5 hours, then warmed slowly to room temperature and stirred for a further 17 hours. The yellow solution was diluted with saturated aqueous ammonium chloride (100 ml) and extracted with ethyl acetate (3×50 ml). The extracts were washed with brine (50 ml), dried (MgSO$_4$), filtered and concentrated. Flash column chromatography on silica, eluting with 40% ethl acetate-hexane, gave the title compound (4.64 g, 64%) as a viscous, colourless oil. $\delta_H$ (360 MHz, CDCl$_3$) 1.45 (9 H, s), 1.47–1.69 (4 H, m), 1.78 (2 H, dd, J=15 and 4), 2.53 (1 H, dd, J=15 and 10), 3.06–3.18 (2 H, m), 3.66 (3 H, s), 3.72–3.85 (2 H, m), 3.86 (2 H, dd, J=10 and 4) and 7.24–7.34 (5 H, m); m/z (ES) 364 (M$^+$+1).

b) 1-tert-Butyloxycarbonyl-4-hydroxy-4-[3-hydroxy-(2-phenyl)propyl]piperidine

A solution of the product of the previous step (3.50 g, 9.63 mmol) in dry THF (50 ml) was added dropwise via cannula to a stirred solution of lithium aluminium hydride (1 M in THF, 20 ml) in dry THF (30 ml) at under nitrogen, cooling the mixture in an ice-bath as necessary to control the mild exotherm. After stirring for 1.5 hours at room temperature the soultion was cooled to 0° C. and aqueous sodium hydroxide (1 M, 5 ml) was added dropwise. The resulting gel was diluted with water (50 mlO and acidified to pH 3–4 with aqueous citric acid (1 M, 50 ml), then extracted with ethyl acetate (3×100 ml). The extracts were washed with brine (50 ml), dried (MgSO$_4$), filtered and concentrated. Dry flash chromatography, eluting with 50% then 66% ethyl acetate-hexane, then ethyl acetate, gave the title compound (2.77 g, 86%) as a colourless glass. $\delta_H$ (360 MHz, CDCl$_3$) 1.44 (9 H, s), 1.45–1.69 (4 H, m), 1.96 (2 H, d, J=9), 3.06–3.21 (3 H, m), 3.66–3.81 (4 H, m) and 7.19–7.37 (5 H, m); m/z (ES) 336 (M$^+$+1).

c) 1-tert-Butyloxycarbonyl-4-hydroxy-4-[3-tosyloxy-(2-phenyl)propyl]piperidine

A solution of the product of the previous step (1.67 g, 4.98 mmol) in dry pyridine (40 ml) under nitrogen was stirred at 0° C. and tosyl chloride (2.37 g, 12.5 mmol) was added in one portion. After stirring for 19 hours at 0° C. the yellow soultion was poured onto crushed ice (150 ml), acidified to pH 5 with aqueous citric acid (1 M, 250 ml) and extracted with diethyl ether (4×100 ml). The extracts were washed with water (100 ml), brine (100 ml), dried (MgSO$_4$), filtered and concentrated. The resulting solid was washed with 5% ethyl acetate-hexane (100 ml) and dried in vacuo to yield the title compound (1.86 g, 76%) as very pale pink granules. δH (360 MHz, CDCl$_3$) 1.25–1.50 (4 H, m), 1.43 (9 H, s), 1.50–1.60 1 H, m), 1.91 (2 H, d, J=6), 2.43 (3 H, s), 2.96–3.16 (2 H, m), 3.21–3.28 (1 H, m) 3.60–3.82 (2 H, m), 4.02–4.11 (2 H, m), 7.14 (2 H, d. J=8), 7.23–7.29 (5 H, m) and 7.65 (2 H, d, J=8); m/z (ES) 490 (M$^+$+1).

d) 1-tert-Butyloxycarbonyl-4-fluoro-4-[3-tosyloxy-(2-phenyl)propyl]piperidine

The title compound (1.08 g, 43%) was prepared from the product of the preceding step (2.51 g, 5.13 mmol) following a similar method to that described for Example 2, step b. $\delta_H$ (250 MHz, CDCl$_3$) 1.17–1.80 (13 H, m) 1.86–2.09 (2 H, m), 2.43 (3 H, s), 2.87–3.04 (2 H, m), 3.16–3.28 (1 H, m), 3.72–3.92 (2 H, m), 4.01 (1 H, dd, J=10 and 7), 4.11 (1 H, dd, J=10 and 7), 7.08–7.12 (2 H, m), 7.22–7.30 (5 H, m) and 7.61–7.65 (2 H, m); m/z (ES) 492 (M$^+$+1).

e) 4-Fluoro-4-[3-fluoro-(2-phenyl)propyl]piperidine

A solution of the product of the previous step (1.00 g, 2.03 mmol) and tetrabutylammonium (triphenylsilyl) difluorosilicate (5.49 g, 10.2 mmol) in dry acetonitrile (30 ml) was refluxed under nitrogen for 64 hours. The mixture was cooled and solvent was removed by evaporation. The residues were triturated with 50% ethyl acetate-hexane and the mixture was filtered. The filtrate was concentrated and partly purified by flash column chromatography on silica, eluting with 15% ethyl acetate-hexane, to give crude 1-tert-butyloxycarbonyl-4-fluoro-4-[3-fluoro-(2-phenyl)propyl] piperidine. The material was dissolved in dichloromethane (4 ml) and trifluoroacetic acid (2 ml) was added. After standing at room temperature for 1.5 hours, solvent and excess acid were removed by evaporation. The residue was dissolved in aqueous sodium hydroxide (1 M, 15 ml) and extracted with dichloromethane (4×10 ml). The extracts were washed with brine (10 ml), dried (MgSO$_4$), filtered and concentrated. Preparative thin layer chromatography on silica, eluting with 90:9:1 dichloromethane-methanol-ammonia, gave the title compound (0.0421 g, 9%) as a colourless oil. $\delta_H$ (250 MHz, CDCl$_3$) 1.23–1.85 (4 H, m), 1.97–2.22 (2 H, m), 2.76–2.92 (4 H, m), 3.22–3.34 (1 H, m), 4.52 (2 H, dd, J=47 and 6) and 7.21–7.46 (5 H, m); m/z (ES) 240 (M$^+$+1).

f) 4-Fluoro-4-[3-fluoro-(2-phenyl)propyl]-1-{3-[5-(1,2,4-triazol-4-yl)-1H-indol-3-yl]propyl}piperidine The title compound free base (0.024 g, 29%) was prepared from Intermediate 1 and the product of the preceding step following a similar method to that described for Example 1, step d. Analytically pure material (2 mg) was isolated by preparative high performance liquid chromatography. $\delta_H$ (360 MHz, CDCl$_3$) 1.25–2.38 (10 H, m), 2.40–2.50 (2 H, m), 2.60–2.76 (2 H, m), 2.77 (2 H, t, J=5), 3.12–3.26 (1 H, m), 4.45 (2 H, dd, J=47 and 6), 7.14 (2 H, dd, J=8 and 2), 7.22–7.26 (3 H, m), 7.30–7.34 (2 H, m), 7.46 (1 H, d, J=9), 7.53 (I H, d, J=2), 8.30 (1 H, s) and 8.45 (2 H, s); m/z (ES) 464 (M$^+$+1).

EXAMPLE 14

4-Fluoro-4-[2-(4-fluorophenyl)ethyl]-1-{3-[5-(1,2,4-triazol-4-yl)-1H-indol-3-yl]propyl}piperidine. Hydrogen Oxalate a) 1-tert-Butoxycarbonyl-4-fluoro-[2-(4-fluorophenyl) ethynyl]piperidine A mixture of 1-tert-butoxycarbonyl-4-ethynyl-4-fluoropiperidine (1 g, 4.4 mmol) and 4-fluoroiodobenzene (610 μl, 5.3 mmol) in N,N-diethylamine (20 ml) was flushed with nitrogen for 15 mins, then palladium bis (tiphenylphosphine)chloride (150 mg, 0.2 mmol) and copper (I) iodide (42 mg, 0.2 mmol) added. The mixture was stirred at room temperature under an atmosphere of nitrogen for 2 hours, then evaporated. The residue was treated with water (50 ml) and extracted with diethyl ether (3×25 ml). The combined organic solutions were washed with water (1×50 ml), brine (1×20 ml), dried (MgSO$_4$) and concentrated. Flash chromatography of the residue (silica gel, ethyl acetate-hexane 1:9) gave 1.3 g (80%) of the title compound: $\delta_H$ (360 MHz, CDCl$_3$) 1.47 (9H, s), 2.01–2.08 (4H, m), 3.51–3.64 (4H, m), 7.00–7.05 (2H, m), 7.42–7.46 (2H, m).

b) 1-tert-Butoxycarbonyl-4fluoro-4-[2-(4-fluorophenyl) ethyl]piperidine

A solution of 1-tert-butoxycarbonyl-4-fluoro-4-[2-(4-fluorophenyl)ethynyl]piperidine in methanol (20 ml) and glacial acid (1 ml) was hydrogenated over 10% Pd-C (0.5 g) at 50 psi for 5 hours. The catalyst was removed by filtration and the solvents removed under vacuum. The residue was dissolved in diethyl ether (20 ml) and washed with saturated aqueous sodium hydrogen carbonate (2×15 ml), dried (MgSO$_4$) and concentrated to give the title product (430 mg, 43%) which was used in the next step without further purification; $\delta_H$ (360 MHz, CDCl$_3$) 1.46 (9H, s), 1.48–1.67 (2H, m), 1.82–1.93 (4H, m), 2.68–2.73 (2H, m), 3.05–3.20 (2H, m), 3.90–3.99 (2H, m), 6.94–6.99 (2H, m), 7.11–7.15 (2H, m): m/z (ES) 326 (M$^+$+1).

c) 4-Fluoro-4-[2-(4-fluorophenyl)ethyl]piperidine

A solution of the product from the preceding step (430 mg, 1.3 mmol) in a mixture of trifluoroacetic acid and dichloromethane (1:2, 9 ml) was allowed to stand at room temperature for 2 hours. Solvents were -removed under vacuum, and the residue treated with saturated aqueous sodium hydrogen carbonate (20 ml) and the product was extracted with dichloromethane (3×15 ml). The combined organic solutions were dried (MgSO$_4$) and concentrated to give 290 mg (97%) of the title compound, which was used in the next step without further purification $\delta_H$ (360 MHz, CDCl$_3$) 1.52–1.71 (2H, m), 1.82–1.92 (4H, m), 2.68–2.73 (2H, m), 2.93–3.00 (4H, m), 6.94–6.99 (2H, m), 7.12–7.16 (2H, m); m/z (ES) 226 (M$^+$+1).

d) 4-Fluoro-4-[2-(4-fluorophenyl)ethyl]1-{3-[5-(1,2,4-triazol-4-yl)-1H-indol-3-yl]propyl}piperidine. Hydrogen Oxalate The title compound free base was prepared from Intermediate 1 and the product from the preceding step following a similar method to that described for Example 1, step d. The oxalate salt was prepared from ethanol-diethyl ether, mp 205° C. (Found: C, 62.38; H, 5.80; N, 12.66. C$_{26}$H$_{29}$F$_2$N$_5$× 1.0C$_2$H$_2$O$_4$ requires: C, 62.33; H, 5.79; N, 12.98%) $\delta_H$ (360 MHz, DMSO-d$_6$) 1.82–2.14 (8H, m), 2.64–2.69 (2H, m), 2.77 (2H, t, J=7.3 Hz), 2.92–3.16 (4H, m), 3.28–3.40 (2H, m), 7.09 (2H, t, J=8.8 Hz), 7.25–7.34 (4H, m), 7.50 (1H, d, J=8.6 Hz), 7.81 (1H, d. J=1.8 Hz), 9.03 (2H, s), 11.20 (1H, bs); m/z (ES) 450 (M$^+$+1). Examples 15–21 were prepared from Intermediate 4 and the appropriate aryl-iodide following a similar procedure to that described for Example 14 (steps a, b, c and d).

EXAMPLE 15

4-Fluoro-4-(2-phenylethyl)-1-{3-[5-(1,2,4-triazol-4-yl)-1H-indol-3-yl]propyl}piperidine. 1.0 Hydrogen Oxalate The oxalate salt was prepared from ethanol-diethyl ether, mp 212° C. (Found: C, 64.05; H, 6.13; N, 13.32. C$_{26}$H$_{30}$FN$_5$×1.0C$_2$H$_2$O$_4$ requires: C, 64.48; H, 6.18; N, 13.43%). $\delta_H$ (360 MHz, DMSO-d$_6$) 1.84–2.14 (8H, m), 2.64–2.69 (2H, m), 2.77 (2H, t, J=7.4 Hz), 2.94–3.12 (4H, m), 3.28–3.40 (2H, m), 7.16–7.34 (7H, m), 7.50 (1H, d, J=8.6 Hz), 7.81 (1H, d, J=1.9 Hz), 9.03 (2H, s), 11.20 (1H, bs); m/z (ES) 432 (M$^+$+1).

EXAMPLE 16

4-Fluoro-4-[2-(2-fluorophenyl)ethyl]-1-{3-[5-(1,2,4-triazol-4-yl)-1H-indol-3-yl]propyl}piperidine. 1.7 Hydrogen Oxalate The oxalate salt was prepared from ethanol-diethyl ether. mp 144° C. (Found: C, 58.72; H, 5.66; N, 11.33. C$_{26}$H$_{29}$F$_2$N$_5$×1.7C$_2$H$_2$O$_4$ requires: C, 58.60; H, 5.42; N, 11.62%). $\delta_H$ (360 MHz, DMSO-d$_6$) 1.84–2.14 (8H, m), 2.69–2.73 (2H, m), 2.75–2.79 (2H, t, J=7.4 Hz), 3.00–310 (4H, m), 3.36–3.44 (2H, m), 7.11–7.16 (2H, m), 7.23–7.29 (1H, m), 7.30–7.38 (4H, m), 7.50 (1H, d, J=8.6 Hz), 7.81 (1H, d. J=1.9 Hz), 9.03 (2H, s), 11.20 (1H, bs); m/z (ES) 450 (M$^+$+1).

EXAMPLE 17

4-Fluoro-4-[2-(2-methoxyphenyl)ethyl]-1-{3-[5-(1,2,4-triazol-4-yl)-1H-indol-3-yl]propyl}piperidine. 1.3 Hydrogen Oxalate The oxalate salt was prepared from ethanol-diethyl ether, mp. 98° C. (Found: C, 61.21; H, 5.87; N, 12.38. C$_{27}$H$_{32}$FN$_5$O×1.3C$_2$H$_2$O$_4$ requires: C, 61.44; H, 6.03; N, 12.10%). $\delta_H$ (360 MHz, DMSO-d$_6$) 1.78–2.15 (8H, m), 2.60– 2.65 (2H, m), 2.78 (2H, t, J=7.2 Hz), 3.00–3.18 (4H, m), 3.34–3.44 (2H, m), 3.77 (3H, s), 6.86 (1H, t, J=7.4 Hz), 6.94 (1H, d, J=7.8 Hz), 7.14–7.20 (2H, m), 7.31–7.35 (2H, m), 7.50 (1H, d, J=8.6 Hz), 7.81 (1H, d, J=1.9 Hz), 9.02 (2H, s), 11.20 (1H, bs); m/z (ES) 462 (M$^+$+1).

EXAMPLE 18

4-Fluoro-4-[2-(2-thienyl)ethyl]-1-{3-[5-(1,2,4triazol-4-yl)-1H-indol-3-yl]propyl}piperidine 1.5 Hydrogen Oxalate The oxalate salt was prepared from ethanol-diethyl ether, mp 211° C. (Found: C, 56.44; H, 5.50; N, 12.46. C$_{24}$H$_{28}$FN$_5$S×1.5C$_2$H$_2$O$_4$ requires: C, 56.63; H, 5.46; N, 12.23%). $\delta_H$ (360 MHz, DMSO-d$_6$) 1.88–2.16 (8H, m), 2.74–2.79 (2H, m), 2.87–2.93 (2H, m), 2.95–3.12 (4H, m), 3.26–3.40 (2H, m), 6.90–6.95 (2H, m), 7.31–7.34 (3H, m), 7.50 (1H, d, J=8.6 Hz), 7.81 (1H, s), 9.03 (2H, s), 11.20 (1H, bs); m/z (ES) 438 (M$^+$+1).

EXAMPLE 19

4-[2-(2-Cyanophenyl)ethyl]-4-fluoro-1-{3-[5-(1,2,4-triazol-4-yl)-1H-indol-3-yl]propyl}piperidine 1.4 Hydrogen Oxalate The oxalate salt was prepared from ethanol-diethyl ether, mp 98° C. (Found: C, 61.42; H, 5.66; N, 14.32. C$_{27}$H$_{29}$FN$_6$× 1.4C$_2$H$_2$O$_4$ requires: C, 61.43; H, 5.50; N, 14.42%). $\delta_H$ (360 MHz, DMSO-d$_6$) 1.88–2.20 (8H, m), 2.72–2.84 (2H, m), 2.84–2.96 (2H, m), 3.00–3.20 (4H, m), 3.34–3.47 (2H, m), 7.32–7.35 (2H, m), 7.42 (1H, t, J=7.5 Hz), 7.49–7.55 (2H, m), 7.65 (1H, t, J=7.3 Hz), 7.78–7.82 (2H, m), 9.03 (2H, s), 11.21 (1H, bs); m/z (ES) 457 (M$^+$+1).

EXAMPLE 20

4-Fluoro-4- [2-(3-methoxyphenyl)ethyl]-1-{3-[5-(1,2,4-triazol-4-yl)-1H-indol-3-yl]propyl}piperidine 1.5 Hydrogen Oxalate The oxalate salt was prepared from ethanol-diethyl ether, mp 164° C. (Found: C, 60.77; H, 5.96; N, 11.65. C$_{27}$H$_{32}$FN$_5$O×1.5C$_2$H$_2$O$_4$ requires: C, 60.39; H, 5.91; N, 11.74%). $\delta_H$ (360 MHz, DMSO-d$_6$) 1.86–2.18 (8H, m), 2.61–2.67 (2H, m), 2.78 (2H, t, J=7.3 Hz), 3.00–3.18 (4H, m), 3.26–3.48 (2H, m), 3.73 (3H, s), 6.75 (1H, d, J=8.4 Hz), 6.80 (2H,m), 7.19 (1H, t, J=8.2 and 8.0 Hz), 7.31–7.35 (2H, m), 7.50 (1H, d, J=8.6 Hz), 7.81 (1H, d, J=1.9 Hz), 9.03 (2H, s), 11.21 (1H, bs); m/z (ES) 462 (M$^+$+1).

EXAMPLE 21

4-Fluoro-4-[2-(3-thienyl)ethyl]-1-{3-[5-(1,2,4-triazol-4-yl)-1H-indol-3-yl]propyl}piperidine 1.1 Hydrogen Oxalate The oxalate salt was prepared from ethanol-diethyl ether. mp 208° C. (Found: C, 58.89; H, 5.81; N, 12.92. C$_{24}$H$_{28}$FN$_5$S×1.1C$_2$H$_2$O$_4$ requires: C, 58.64; H, 5.67; N, 13.05%). $\delta_H$ (360 MHz, DMSO-d$_6$) 1.98–2.18 (8H, m), 2.66–2.71 (2H, m), 2.77 (2H, t, J=7.4 Hz), 2.94–3.16 (4H, m), 3.28–3.41 (2H, m), 7.02 (1H, d, J=4.9 Hz), 7.20 (1H, s), 7.30–7.34 (2H, m). 7.44 (1H, dd, J=4.9 and 2.9 Hz), 7.50 (1H, d, J=8.6 Hz), 7.81 (1H, d, J=1.7 Hz), 9.03 (2H, s), 11.22 (1H, bs); m/z (ES) 438 (M$^+$+1).

We claim:

1. A compound of formula I, or a salt thereof:

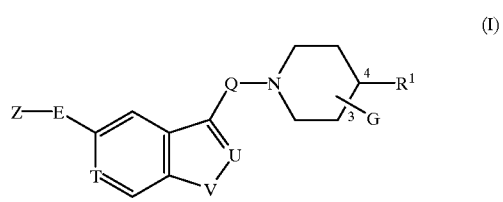

wherein

Z represents 1,2,4-triazole, which is optionally substituted with C$_{1-6}$alkyl, C$_{2-6}$, alkenyl, C$_{2-6}$alkynyl, $C_{3-7}$cycloalkyl, aryl, aryl($C_{1-6}$)alkyl, $C_{1-6}$alkoxy, $C_{1-6}$alkylthio, amino, $C_{1-6}$alkylamino, di($C_{1-6}$)alkylamino, halogen, cyano or trifluoromethyl, wherein aryl is phenyl or naphthyl, E represents a chemical bond or a straight or branched alkylene chain containing from 1 to 4 carbon atoms;

Q represents a straight or branched alkylene chain containing from 1 to 6 carbon atoms, optionally substituted in any position by one or more substituents selected from fluoro and hydroxy;

T represents CH;

U represents C-$R^2$;

V represents N-$R^3$;

G is attached at position 3 or 4 of the piperidine ring and represents halogen or $C_{1-6}$ alkoxy;

$R^1$ represents $C_{3-6}$ alkenyl, $C_{3-6}$ alkynyl, or aryl($C_{1-6}$) alkyl wherein aryl is phenyl or naphthyl, any of which groups may be optionally substituted with one or more substituents selected from halogen, cyano, trifluoromethyl, $C_{1-6}$alkoxy, amino, di($C_{1-6}$)alkylamino, di($C_{1-6}$)alkylaminomethyl, $C_{2-6}$alkylcarbonylamino, $C_{2-6}$alkoxycarbonylamino, N-($C_{1-6}$)alkyl-N-($_{2-6}$)alkoxycarbonylamino, $C_{1-6}$alkylsulphonylamino, aminocarbonylamino, aminocarbonyl, $C_{1-6}$alkylaminocarbonyl, di($C_{1-6}$)alkylaminocarbonyl, aminosulphonyl, di($C_{1-6}$)alkylaminosulphonyl and $C_{1-6}$ alkylaminosulphonylmethyl; and $R^2$ and $R^3$ independently represent hydrogen or $C_{1-6}$alkyl.

2. 4-Benzyl-4-fluoro-1-[3-(5-(1,2,4-triazol-4-yl)-1H-indol-3-yl)propyl]piperidine;
4-fluoro-4-[2-(3-fluorophenyl)ethyl]-1-[3-(5-(1,2,4-triazol-4-yl)-1H-indol-3-yl)propyl]piperidine;
4-fluoro-(3-fluorobenzyl)-1-[3-(5-(1,2,4-triazol-4-yl)-1H-indol-3-yl)propyl]piperidine;
4-fluoro-4-(2-fluorobenzyl)-1-[3-(5-(1,2,4-triazol-4-yl)-1H-indol-3-yl)propyl]piperidine;
4-benzyl-4-methoxy-1-[3-(5-(1,2,4-triazol-4-yl)-1H-indol-3-yl)propyl]piperidine;
4-benzyl-4-methoxy-1-[3-(5-(1,2,4-triazol-1-ylmethyl)-1H-indol-3-yl)propyl]piperidine;
4-(2-fluorobenzyl)-4-methoxy-1-[3-(5-(1,2,4-triazol-4-yl)-1H-indol-3-yl)propyl]piperidine;
4-(3-fluorobenzyl)-4-methoxy-1-[3-(5-(1,2,4-triazol-4-yl)-1H-indol-3-yl)propyl]piperidine;
4-(4-fluorobenzyl)-4-methoxy-1-[3-(5-(1,2,4-triazol-4-yl)-1H-indol-3-yl)propyl]piperidine;
4-fluoro-4-[2-(trifluoromethyl)benzyl]-1-{3-[5-(1,2,4-triazol-4-yl)-1H-indol-3-yl]propyl}piperidine;
4-fluoro-4-[2-(N,N-dimethylaminosulfonyl)benzyl]-1-{3-[5-(1,2,4-triazol-4-yl)-1H-indol-3-yl]propyl}piperidine;
4-fluoro-4-(2-phenylpropyl)-1-{3-[5-(1,2,4-triazol-4-yl)-1H-indol-3-yl]propyl}piperidine;
4-fluoro-4-[3-fluoro-(2-phenyl)propyl]-1-{3-[5-(1,2,4-triazol-4-yl)-1H-indol-3-yl]propyl}piperidine;
4-fluoro-4-[2-(4-fluorophenyl)ethyl]-1-{3-[5-(1,2,4-triazol-4-yl)-1H-indol-3-yl]propyl}piperidine;
4-fluoro-4-(2-phenylethyl)-1-{3-[5-(1,2,4-triazol-4-yl)-1H-indol-3-yl]propyl}piperidine;
4-fluoro-4-[2-(2-fluorophenyl)ethyl]-1-{3-[5-(1,2,4-triazol-4-yl)-1H-indol-3-yl]propyl}piperidine;
4-fluoro-4-[2-(2-methoxyphenyl)ethyl]-1-{3-[5-(1,2,4-triazol-4-yl)-1H-indol-3-yl]propyl}piperidine;
4-[2-(2-cyanophenyl)ethyl]-4-fluoro-1-{3-[5-(1,2,4-triazol-4-yl)-1H-indol-3-yl]propyl}piperidine; or
4-fluoro-4-[2-(3-methoxyphenyl)ethyl]-1-{3-[5-(1,2,4-triazol-4-yl)-1H-indol-3-yl]propyl}piperidine;

or a salt thereof.

3. A pharmaceutical composition comprising an effective amount of a compound according to claim 1, or pharmaceutically acceptable salt thereof, and a pharmaceutically acceptable carrier.

4. A method of treatment of a subject suffering from migraine and associated conditions, which comprises administering to that subject a therapeutically effective amount of a compound according to claim 1 thereof.

5. A method of treatment of a subject suffering from migraine and associated conditions, which comprises administering to that subject a therapeutically effective amount of a compound according to claim 2 or a therapeutically acceptable salt thereof.

* * * * *